(12) United States Patent
Heindl et al.

(10) Patent No.: US 7,759,469 B2
(45) Date of Patent: Jul. 20, 2010

(54) LABELING REAGENT

(75) Inventors: Dieter Heindl, Paehl (DE); Thomas Froehlich, Bichl (DE); Heribert Maerz, Paehl (DE); Monika Seller, Benediktbeuern (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/370,527

(22) Filed: Mar. 8, 2006

(65) Prior Publication Data

US 2006/0216736 A1 Sep. 28, 2006

(30) Foreign Application Priority Data

Mar. 10, 2005 (EP) .................................. 05005221

(51) Int. Cl.
- C07G 3/00 (2006.01)
- C07H 21/00 (2006.01)
- C12Q 1/68 (2006.01)

(52) U.S. Cl. ...................... 536/4.1; 536/23.1; 536/26.6; 536/25.3; 435/6

(58) Field of Classification Search .................. 536/4.1, 536/23.1, 26.6, 25.3; 435/6
See application file for complete search history.

(56) References Cited

U.S. PATENT DOCUMENTS

| | | | |
|---|---|---|---|
| 5,118,801 A | 6/1992 | Lizardi et al. | |
| 5,130,238 A | 7/1992 | Malek et al. | |
| 5,141,837 A | 8/1992 | Nguyen et al. | |
| 5,270,184 A | 12/1993 | Walker et al. | |
| 5,455,166 A | 10/1995 | Walker | |
| 5,494,810 A | 2/1996 | Barany et al. | |
| 5,538,848 A | 7/1996 | Livak et al. | |
| 5,871,908 A | 2/1999 | Henco et al. | |
| 5,994,056 A | 11/1999 | Higuchi | |
| 6,004,286 A | 12/1999 | Bellhouse et al. | |
| 6,174,670 B1 | 1/2001 | Wittwer et al. | |
| 6,355,437 B1 | 3/2002 | Neri et al. | |
| 2003/0022177 A1 | 1/2003 | Wittwer et al. | |

FOREIGN PATENT DOCUMENTS

| | | |
|---|---|---|
| EP | 0122614 B1 | 10/1984 |
| EP | 0439182 B1 | 4/1996 |

(Continued)

OTHER PUBLICATIONS

Abramson, R. et al., "Nucleic acid amplification technologies," Current Opinion in Biotechnology 1993, 4;41-47.

(Continued)

*Primary Examiner*—Jezia Riley
(74) *Attorney, Agent, or Firm*—Marilyn L. Amick; Roche Diagnostics Operations, Inc.

(57) ABSTRACT

The current invention restates substituted nitroindole nucleosides as both terminal as well as internal building blocks of labeled oligonucleotide probes for the detection, analysis and quantitation of nucleic acids. The substituent comprises a linker and a detectable group or a linker and a reactive group for post synthesis coupling. These modified nucleosides grant access to a wide application area. These new substituted nitroindole nucleosides can be used as labeling reagents for the facile preparation of, e.g., optimized hybridization probes, simple probes, TAQMAN-probes or molecular beacon probes.

20 Claims, 4 Drawing Sheets

FOREIGN PATENT DOCUMENTS

| WO | WO 84/03285 | 8/1984 |
|----|----|----|
| WO | WO 90/01069 | 2/1990 |
| WO | WO 92/08808 | 5/1992 |
| WO | WO 97/46707 | 12/1997 |
| WO | WO 97/46712 | 12/1997 |
| WO | WO 97/46714 | 12/1997 |
| WO | WO 02/14555 A2 | 2/2002 |
| WO | WO 2004/111072 A2 | 12/2004 |

OTHER PUBLICATIONS

Barany, F., "Genetic disease detection and DNA amplification using cloned thermostable ligase," Proc. Natl. Acad. Sci. USA, vol. 88 (Jan. 1991) 189-193.

Barany, F., "The Ligase Chain Reaction in a PCR World," PCR Methods Appl. 1 (1991) 5-16.

Beaucage, S. et al., "Deoxynucleoside Phosphoradites—A New Class of Key Intermediates for Deoxypolynucleotide Synthesis," Tetrahedron Letters, vol. 22, No. 20, pp. 1859-1862, 1981.

Beaucage, S., Oligodeoxyribonucleotides Synthesis, in: Methods in Molecular Biology, vol. 20, Humana Press, Totowa, N.J. (1993).

Bernard, P. et al., "Integrated Amplification of Detection f the C677T Point Mutation in the Methylenetrahydrofolate Reductase Gene by Fluorescence Resonance Energy Transfer and Probe Melting Curves," Analytical Biochemistry 255, 101-107 (1998) Article No. AB972427.

Bieche, I, et al. "Quantitation of MYC Gene Expression in Sporadic Breast Tumors with Real-Time Reverse Transcription-PCR Assay," Cancer Research 59 (1999) 2759-2765.

Dubey, I. et al., "Modification of the Thiourea Linkage of a Fluorescein-Oligonucleotide Conjugate to a Guanidinium Motif during Ammonia Deprotection," Bioconjugate Chem. 1998, 9, 627-632.

Dueholm, K. et al., "Synthesis of Peptide Nucleic Acid Monomers Containing the Four Natural Nucleobases: Thymine, Cytosine, Adenine, and Guanine and Their Oligomerization," J. Org. Chem. 1994, 59, 5767-5773.

Gait, M. J., Oligonucleotide Synthesis: A Practical Approacy ed., IRL Press (1984).

Gibson, U. et al., "A Novel Method for Real Time Quantitative RT-PCR," Genome Res. 6 (1996) 995-1001.

Greene, T. et al., (eds) Protective Groups in Organic Chemistry, $3^{rd}$ Ed., John Wiley & Sons, New York, NY 1999.

Guatelli, J. et al., "Isothermal, in vitro amplification of nucleic acids by a multienzyme reaction modeled after retroviral replication," Proc. Natl. Acad. Sci. USA, vol. 87, pp. 1874-1878, Mar. 1990.

Higuchi, R. et al., "Simultaneous Amplification and Detection of Specific DNA Sequences," Bio/technology, vol. 10, Apr. 1992, 413-417.

Kuijpers, W. et al., "Synthesis of well-defined phosphate-methylated DNA fragments: the application of potassium carbonate in methanol as deprotecting reagent," Nucleic Acids Research, vol. 18, No. 17, pp. 5197-5205, 1990.

Kwoh, D. et al., "Transcription—based amplification system and detection of amplified human immunodeficiency virus type 1 with a bead-based sandwich hybridization format," Proc. Natl. Acad. Sci. USA, vol. 86, pp. 1173-1177, Feb. 1989.

Letsinger, R. et al., "Their Organic Derivatives," Journal of the American Chemical Society 91:12, Jun. 4, 1969, 3360-3365.

Loakes, D. et al., "5-Nitroindole as an universal base analogue," Nucleic Acid Research, vol. 22, No. 20, 1994, p. 4039-4043.

Loakes, D., "Survey and Summary: The application s of universal DNA base analogues," Nucleic Acids Research, 2001, vol. 29, No. 12, p. 2437-2447.

Matthews, J. et al., "REVIEW Analytical Strategies for the Use of DNA Probes," Analytical Biochemistry 169, 1-25 (1988).

McBride, L. et al., "An Investigation of Several Deoxynucloside Phosphoramidites Useful for Synthesizing Deoxyoligonucleotides," Tetrahedron Letters, vol. 24, No. 3, pp. 245-248 (1983).

Nichols, R., et al., "A universal nucleoside for use at ambiguous sites in DNA primers," Nature, vol. 369, Jun. 9, 1994, p. 493-493.

Revankar, G. et al., "The Synthesis and PMR Study of Certain 3-Substituted 2-(β-D-Ribofuranosyl) indazoles (1a)," Heterocycl. Chem. 7 (1970) 1329-1332.

Seela, F. et al., "44.Synthesis of 4-Substituted 1H-Benzimidazole 2'-Deoxyribonuclosides and Utility of the 4-Nitro Compound an Universal Base," Helvetica Chimica Acta, vol. 79 (1996) p. 488-498.

Shimada, M. et al., "The Isothermal and Chimeric Primer-Initiated Amplification of Nucleic Acids (ICAN)," Rinsho Byori, 51 (2003)1061-1067.

Thomas, D. et al., "Amplification of Padlock Probes for DNA Diagnostics by Cascade Rolling Circle Amplification or the Polymerase Chain Reaction," Arch Pathol Lab Med., vol. 123, p. 1170-1176, Dec. 1999.

Verma, S. et al., "Modified Oligonucleotieds: Synthesis and Strategy for Users," Annu. Review, Biochem., 1998 67:99-134.

Walton, T. et al., "Evaluation of New Linkers and Synthetic Methods for Internal Modified Oligonucleotides," Bioconjugate Chem., vol. 13, No. 5, 2002, p. 1155-1158.

Whelen, A. et al., "The Role of Nucleic Acid Amplification and Detection in the Clinical Microbiology Laboratory," Annu. Rev. Microbiol. 1996, 50:349-373.

Wojczewski, C. et al., "Fluorescent Oligonucleotides—Versatile Tools as Probes and Primers for DNA and RNA Analysis," Synlett 1999, No. 10, 1667-1678.

Wu, D., et al., "The Ligation Amplification Reaction (LAR)—Amplification of Specific DNA Sequences Using Sequential Rounds of Template-Dependent Ligation," Genomics 4, 560-569 (1989).

Zimmermann, K. et al., "Technical Aspects of Quantitative Competitive PCR," BioTechniques, vol. 21, No. 2 (1996) 268-279.

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial sequence
<220> FEATURE:
<223> OTHER INFORMATION: PCR-primer sense for Genotyping of the MDR-1
      C3435T Polymorphism

<400> SEQUENCE: 1
gatctgtgaa ctcttgtttt ca                                           22

<210> SEQ ID NO 2
<211> LENGTH: 24
<212> TYPE: DNA
<213> ORGANISM: Artificial sequence
<220> FEATURE:
<223> OTHER INFORMATION: PCR-primer antisense for Genotyping of the
      MDR-1 C3435T Polymorphism

<400> SEQUENCE: 2
tttgaagaga gacttacatt aggc                                         24

<210> SEQ ID NO 3
<211> LENGTH: 23
<212> TYPE: DNA
<213> ORGANISM: Artificial sequence
<220> FEATURE:
<223> OTHER INFORMATION: Single labelled detector probe for Genotyping
      of the MDR-1 C3435T Polymorphism
<220> FEATURE:
<221> NAME/KEY: modified_base
<222> LOCATION: (1)..(1)
<223> OTHER INFORMATION: 1-(2-deoxy-beta-D-ribofuranosyl)-5-nitroindole
<220> FEATURE:
```

```
<221> NAME/KEY: misc_feature
<222> LOCATION: (1)..(1)
<223> OTHER INFORMATION: n is a, c, g, or t

<400> SEQUENCE: 3
ntcacaggaa gagatcgtga ggg                                              23

<210> SEQ ID NO 4
<211> LENGTH: 22
<212> TYPE: DNA
<213> ORGANISM: Artificial sequence
<220> FEATURE:
<223> OTHER INFORMATION: SLP 1
<220> FEATURE:
<221> NAME/KEY: modified_base
<222> LOCATION: (7)..(7)
<223> OTHER INFORMATION: 1-(2-deoxy-beta-D-ribofuranosyl)-5-nitroindole
      functionalised with 6-Carboxyfluoresceine
<220> FEATURE:
<221> NAME/KEY: misc_feature
<222> LOCATION: (7)..(7)
<223> OTHER INFORMATION: n is a, c, g, or t

<400> SEQUENCE: 4
tcacagnaag agatcgtgag gg                                               22

<210> SEQ ID NO 5
<211> LENGTH: 22
<212> TYPE: DNA
<213> ORGANISM: Artificial sequence
<220> FEATURE:
<223> OTHER INFORMATION: SLP 2
<220> FEATURE:
<221> NAME/KEY: modified_base
<222> LOCATION: (9)..(9)
<223> OTHER INFORMATION: 1-(2-deoxy-beta-D-ribofuranosyl)-5-nitroindole
      functionalised with 6-Carboxyfluoresceine
<220> FEATURE:
<221> NAME/KEY: misc_feature
<222> LOCATION: (9)..(9)
<223> OTHER INFORMATION: n is a, c, g, or t

<400> SEQUENCE: 5
tcacaggang agatcgtgag gg                                               22
```

LABELING REAGENT

RELATED APPLICATIONS

This application claims priority to European application EP 05005221.6 filed Mar. 10, 2005.

FIELD OF THE INVENTION

The current invention restates substituted nitroindole nucleosides as both terminal as well as internal building blocks of labeled oligonucleotide probes for the detection, analysis and quantification of nucleic acids. The substituent comprises a linker and a detectable group or a linker and a reactive group for post synthesis coupling. These modified nucleosides grant access to a wide application area. These new substituted nitroindole nucleosides can be used as labeling reagents for the facile preparation of, e.g., optimized hybridization probes, simple probes, TAQMAN probes or molecular beacon probes.

BACKGROUND OF THE INVENTION

The steady increase in the number of decoded and mapped genomic sequences from flora and fauna is an impressive demonstration how important DNA-techniques are nowadays. But not the mere sequencing of DNA is of importance. With increasing knowledge in the field of genomics and proteomics, the impact of specific effects, e.g., mutations, on the future of cells or organisms comes into the focus of scientists. Since on the one hand, the nucleic acids are often present in very small concentrations and, on the other hand, they are often found in the presence of many other solid and dissolved substances, e.g., after lysis of cells, they are difficult to isolate or to measure.

Diverse methods for the detection, analysis and quantitation by hybridization of the target nucleic acid with a detectable probe have been established (e.g., Southern hybridization, dot blotting, gel-assays, PCR).

The main tool of nucleic acid related work, e.g., for amplification of polymeric nucleic acids, is the polymerase chain reaction (PCR). In recent years the knowledge about and the applications of PCR were noticeably expanded.

A PCR procedure consists in general of three steps: sample preparation, amplification, and product analysis. Although these steps are usually performed sequentially, amplification and analysis can occur simultaneously. DNA dyes or fluorescent probes can be added to the PCR mixture before amplification and used to analyze PCR products during amplification. The concurrent amplification and analysis of the sample within the same tube without changing the instrument reduces sample handling time, and minimizes the risk of product contamination for subsequent reactions. This approach of combining amplification with analysis has become known as "real time" PCR (U.S. Pat. No. 6,174,670).

Other possible amplification reactions are the Ligase Chain Reaction (LCR, Wu, D. Y., and Wallace, R. B., Genomics 4 (1989) 560-569; and Barany, F., Proc. Natl. Acad. Sci. USA 88 (1991) 189-193; U.S. Pat. No. 5,494,810); Polymerase Ligase Chain Reaction (Barany, F., PCR Methods Appl. 1 (1991) 5-16); Gap-LCR (PCT Patent Publication No. WO 90/01069; U.S. Pat. No. 6,004,286); Repair Chain Reaction (European Patent Publication No. 439 182 A2); 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; PCT Patent Publication No. WO 92/08808); and NASBA (U.S. Pat. No. 5,130,238). Further, there are strand displacement amplification (SDA, U.S. Pat. No. 5,270,184; U.S. Pat. No. 5,455,166), transcription mediated amplification (TMA) and Q-beta-amplification (for a review see, e.g., Whelen, A. C., and Persing, D. H., Annu. Rev. Microbiol. 50 (1996) 349-373; Abramson, R. D., and Myers, T. W., Curr. Opin. Biotechnol. 4 (1993) 41-47), as well as isothermal and chimeric primer-initiated amplification of nucleic acids (ICAN, Shimada, M., et al., Rinsho Byori. 51 (2003) 1061-1067) and cascade rolling circle amplification (CRCA, Thomas, D. C., et al., Arch. Pathol. Lab. Med. 123 (1999) 1170-1176).

For the above mentioned nucleic acid technique synthetic (deoxy)-oligonucleotides which have been provided with a detectable label are necessary, e.g., to carry out a broad spectrum of diverse molecular biological and molecular diagnostic methods.

Methods for the synthesis of single stranded oligonucleotide and oligonucleotide analogue sequences are known from the art (e.g., Oligonucleotide Synthesis: A Practical Approach, Gait, ed., IRL Press, Oxford (1984); Kuijpers, W. H. A., et al., Nucleic Acids Research 18 (1990) 5197-5205; Dueholm, K. L., J. Org. Chem. 59 (1994) 5767-5773; Agrawal, S. (ed.), Methods in Molecular Biology, volume 20).

The first effective and widely applicable method for the synthesis of oligo- and polynucleotides was the phosphotriester method (see, e.g., Letsinger, R. L., et al., JACS 91 (1969) 3360-3365). In this method the phosphate backbone of the synthesized polynucleic acid is already present. To prevent side reactions like branching during the synthesis reactive groups were protected with, e.g., the beta-cyanoethyl group or the ortho-chlorphenyl group. As activator for the coupling step mesityl sulfonyl chloride and mesityl sulfonyl nitrotriazole have been used.

Synthetic (deoxy)-oligonucleotides are usually prepared on a solid phase with the aid of phosphoramidite chemistry. Glass beads having pores of a defined size (abbreviated in the following as CPG, controlled pore glass) are usually used as the solid phase. The first monomer is bound to the support via a cleavable group such that the oligonucleotide can be set free by cleavage of this group after the solid phase synthesis is completed. The first monomer additionally contains a protected hydroxyl group, whereas dimethoxytrityl (DMT) is usually utilized as the protective group. The protective group can be removed by acid treatment. Then 3'-phosphoramidite derivatives of (deoxy)-ribonucleosides that are also provided with a DMT protective group are coupled in a cyclic process to each successive reactive group after is has been freed of the DMT protective group.

According to the prior art so-called trifunctional support materials are used to prepare oligonucleotides that are labeled at the 3' end. For this a trifunctional spacer with two reactive hydroxyl groups and an additional reactive group, preferably an amino group, is firstly prepared. After introducing a DMT protective group on a hydroxyl group, the detectable label is coupled to the reactive amino group of the trifunctional spacer in a second step of the synthesis. However, alternatively the detectable label is not only coupled to the trifunctional spacer via a reactive amino group but also via a third hydroxyl group or an SH group (U.S. Pat. No. 5,451,463, WO 92/11388). In a third step the trifunctional spacer is bound via its hydroxyl group that is still free to the linking group of the solid phase material that is provided with a cleavable bond.

Alternatively the detectable label is not coupled until after the actual oligonucleotide synthesis (U.S. Pat. No. 5,141, 837). However, since this requires multiple independent coupling reactions, such a production process is laborious, costly and cannot be automated.

Labeled phosphoramidites, in which the marker group is linked to the phosphoramidite via a C3-12 ($C_3$-$C_{12}$) linker, are usually used to synthesize oligonucleotides labeled at the 5' end.

Hence detectable labels can also be introduced internally by the phosphoramidite strategy (Wojczewski, C., et al., Synlett 10 (1999) 1667-1678). The same trifunctional spacers can be used for this as for the synthesis of CPG materials. Instead of binding one of the hydroxyl groups to the solid phase, this hydroxyl group is converted into a phosphoramidite in this process. The resulting phosphoramidite can be used for oligonucleotide synthesis like a standard amidite. In principle such phosphoramidites can also be used for internal labeling by replacing a standard nucleoside phosphoramidite by a fluorophore-labeled phosphoramidite during the synthesis cycle. However, it is preferably used for 5' labeling since internal labeling interrupts the base pairing in the strand.

Oligonucleotides provided with a fluorescent label such as fluorescein are often used in molecular biology, such as for the real-time measurement of PCR reactions (WO 97/46707). The fluorescent dyes can be coupled to, e.g., the amino group of the trifunctional spacer in different ways according to the prior art.

On the one hand the fluorescent dye, which can itself optionally be provided with cleavable protective groups for protection during the oligonucleotide synthesis, is reacted in the form of an isothiocyanate with the amino group to form a thiourea bond. In an alternative process the N-hydroxy-succinimide ester (NHS-ester) of a fluorophore-carboxylic acid is reacted with the free amino group of the spacer to form an amide bond. Alternatively the linker is terminated with a carboxyl group and is then reacted with an aminomodified label.

Beside these chemical methods for the preparation of labeled oligonucleotides enzymatic methods are available. For example a terminal label can be introduced using the enzyme terminal deoxynucleotidyl transferase which introduces an additional nucleotide at the end of an existing polydeoxynucleotide chain. This enzymatically introduced nucleotide bears the signal entity (see, e.g., EP 0122614).

The great success of real-time methods is closely linked to the detection or change of a reporter signal. This signal change evolves from the interaction of the probe molecule with the target molecule.

Monitoring fluorescence during each cycle of PCR initially involved the use of ethidium bromide (Higuchi, R., et al., Bio/Technology 10 (1992) 413417; Higuchi R., et al., Bio/Technology 11 (1993) 1026-1030; U.S. Pat. No. 5,994,056). In that system fluorescence is measured once per cycle as a relative measure of product concentration. Ethidium bromide detects double stranded DNA; if the template is present, fluorescence intensity increases with temperature cycling. Other fluorescent systems have been developed that are capable of providing additional data concerning the nucleic acid concentration and sequence.

In kinetic real time PCR, the formation of PCR products is monitored in each cycle of the PCR. The amplification is usually measured in thermocyclers which have additional devices for measuring fluorescence signals during the amplification reaction. In general, there exist different formats for real time detection of amplified DNA, of which the following are well known and commonly used in the art:

DNA binding dye format: Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like Sybr Green I, for example, do not affect the efficiency of the PCR reaction (U.S. Pat. No. 6,174,670).

All other formats known in the art require the design of a fluorescent labeled hybridization probe which only emits fluorescence upon binding to its target nucleic acid.

TAQMAN probe: A single-stranded hybridization probe is labeled with two components. When the first component is excited with light of a suitable wavelength, the absorbed energy is transferred to the second component, the so-called quencher, according to the principle of fluorescence resonance energy transfer (FRET). During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured (U.S. Pat. No. 5,538,848).

Molecular Beacons: These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

FRET hybridization probes: The FRET hybridization probe test format is especially useful for all kinds of homogenous hybridization assays (Matthews, J. A., and Kricka, L. J., Anal. Biochem. 169 (1988) 1-25). It is characterized by a pair of two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound.

Besides PCR and real time PCR, FRET hybridization probes and molecular beacons are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively, i.e. continuously, increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed. Alternatively it is possible to use a fluorescent-labeled primer and only one labeled oligonucleotide probe (Bernard, P. S., et al., Anal. Biochem. 235 (1998) 101-107).

Single label probe (SLP) format: This detection format consists of a single oligonucleotide labeled with a single fluorescent dye at either the 5'- or 3'-end (WO 02/14555). Two different designs can be used for oligonucleotide labeling, G-quenching probes and nitroindole-dequenching probes.

In the G-quenching embodiment, the fluorescent dye is attached to a C at the 5'- or 3'-end of the oligonucleotide. Fluorescence decreases significantly when the probe is hybridized to the target, in case two G's are located on the target strand opposite to C and in position 1 aside of the complementary oligonucleotide probe.

In the nitroindole dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

In US patent application US 2003/0022177, Wittwer et al. principally introduced base analogs for the modification of the terminal ends of probe oligonucleotides. The corresponding labeled probe oligonucleotides showed the same performance as conventional oligonucleotide probes without base analogs, i.e. fluorescence increase upon hybridization with the target nucleotide sequence and fluorescence decrease after dissociation. Dequenching probes containing base analogs have been named but neither their synthesis nor their detailed characteristics have been described.

PCR products can be quantified in two fundamentally different ways.

End point determination of the amount of PCR product formed in the plateau phase of the amplification reaction: In this case the amount of PCR product formed does not correlate with the amount of the initial copy number since the amplification of nucleic acids at the end of the reaction is no longer exponential and instead saturation is reached. Consequently different initial copy numbers exhibit identical amounts of PCR product formed. Therefore the competitive PCR or competitive RT-PCR method is usually used in this procedure. In these methods the specific target sequence is coamplified together with a dilution series of an internal standard of a known copy number. The initial copy number of the target sequence is extrapolated from the mixture containing an identical PCR product quantity of standard and target sequence (Zimmermann, K., and Mannhalter, J. W., BioTechniques 21 (1996) 280-279). A disadvantage of this method is also that measurement occurs in the saturation region of the amplification reaction.

Kinetic real-time quantification in the exponential phase of PCR: In this case the formation of PCR products is monitored in each cycle of the PCR. The amplification is usually measured in thermocyclers which have additional devices for measuring fluorescence signals during the amplification reaction. A typical example of this is the Roche Diagnostics LightCycler (Cat. No. 2 0110468). The amplification products are for example detected by means of fluorescent labeled hybridization probes which only emit fluorescence signals when they are bound to the target nucleic acid or in certain cases also by means of fluorescent dyes that bind to double-stranded DNA. A defined signal threshold is determined for all reactions to be analyzed and the number of cycles required to reach this threshold value is determined for the target nucleic acid as well as for the reference nucleic acids such as the standard or housekeeping gene. The absolute or relative copy numbers of the target molecule can be determined on the basis of these values obtained for the target nucleic acid and the reference nucleic acid (Gibson, U. E., et al., Genome Res. 6 (1996) 995-1001; Bieche, I., et al., Cancer Res. 59 (1999) 2759-2765; WO 97/46707; WO 97/46712; WO 97/46714). Such methods are also referred to as a real-time PCR.

For synthesizing nucleic acid probes several compounds and their use for incorporation as monomeric units into nucleic acids are known in the art. Such compounds provide functional groups and/or linking moieties for the covalent attachment of reporter groups or labels. In the course of the chemical synthesis of the oligomeric compound, the skeletal structure of the "non-nucleotide compound" or "modified nucleotide" is connected with the "oligonucleotide" backbone, for example by phosphoramidite-based chemistry resulting in a phosphodiester. A given incorporated compound thus represents a modified nucleotide within the newly generated "modified oligonucleotide". A label is bound by a functional group, exemplified by, but not limited to, an amino function that is present on the skeletal structure proper or on the "linking moiety", which connects the skeleton with the functional group. A label can be covalently attached to the compound prior to the synthesis of a "modified oligonucleotide" or afterwards, upon the removal of an optional protecting group from the functional group to which the label is to be coupled.

EP 0135587 describes modifications of conventional nucleosides which carry a reporter group attached to a substituent group of the nucleotide base. EP 0313219 discloses non-nucleoside reagents characterized by a linear hydrocarbon skeletal structure with a linking moiety, or a side group, to which a label can be bound. EP 0313219 is silent about other types of skeletal structures and their particular properties.

U.S. Pat. No. 5,451,463 describes trifunctional non-nucleotide reagents, particularly 1,3-diol-based skeletal structures possessing a primary amino group. Such reagents can be used for example for terminal labeling of 3' termini of oligonucleotides. WO 97/43451 discloses non-nucleotide reagents based on a carbocyclic ($C_5$ to $C_7$) skeletal structure, whereby a substituted or unsubstituted cyclohexane is preferred.

In summary, this technologies are either based on non-nucleosidic linkers/monomeric compounds which upon internally incorporation result in disruption of the probe structure or on modifications of a specific nucleobase, which requires for flexible internal labeling the synthesis of four different phosphoramidites.

Thus, it was the object of the present invention to overcome the afore described problems by providing an alternate labeling system which allows for an easy as well as position and dye independent labeling. In another aspect, the objective of the present invention was to provide improved probes for nucleic acid amplification, detection and quantitation.

SUMMARY OF THE INVENTION

Thus, the invention is directed to a new, universally applicable, detectable compound for nucleic acid probes. The compound comprises a nucleoside with a modified universal base as nucleobase. This nucleoside shows improved synthetic and detection properties.

More precisely, the invention comprises the synthesis and use of a nucleoside with a 3-substituted nitroindole as nucleobase. By incorporating this nucleoside as universal nucleoside into an oligonucleotide, labeling, terminal as well as internal, can be accomplished. Therefore a position independent labeling of oligonucleotides and as a result of PCR probes can be carried out. Beside improved synthetic properties, among other things, a noticeably increased signal to noise ratio in different detection formats can be achieved.

This universally applicable nucleoside can be incorporated at any position of an oligonucleotide. Thus, in case of a dye stable during oligonucleotide synthesis, no post synthesis labeling is required. Additionally, for dyes unstable during oligonucleotide synthesis, a reactive group can be attached to the nitroindole based nucleobase for post-synthesis labeling.

The present invention comprises compounds having the structure/formula I:

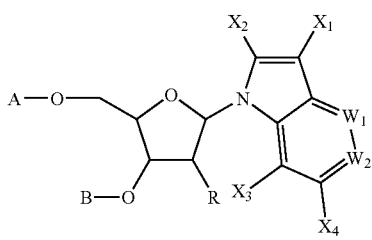

characterized in that A and B are independent from each other and independent from R, $X_1$, $X_2$, $X_3$, $X_4$ and $W_1$ and $W_2$ and whereby A and B are selected from the group consisting of (1) hydrogen, (2) a protecting group, (3) a solid phase with a linker, (4)a phosphoramidite, (5) an H-phosphonate, (6) a triphosphate, (7) a phosphate, and (8) a chain of nucleotide residues, with the proviso that A but not B is a triphosphate, with the proviso that if one of A or B is a phosphoramidite or a H-phosphonate, the other of A and B is a protective group and R is not OH, with the proviso that only one of A and B is a solid phase with a linker, R=H, OH, O-alkyl, O-alkenyl, O-alkinyl, O-protective group, or F, one of $W_1$, $W_2$=C—$NO_2$, and the other of $W_1$, $W_2$ is CH or N, one of $X_1$, $X_2$, $X_3$, $X_4$ is either a reactive group or a protected reactive group or a linker with a reactive group or a linker with a protected reactive group or a signal entity or a protected signal entity or a linker with a signal entity or a linker with a protected signal entity, and the three others are H.

One embodiment of the current invention is an oligonucleotide comprising a compound of formula I.

Another embodiment of the current invention is an oligonucleotide comprising at least two signal entities based on a compound of formula I.

Another embodiment of the current invention is a labeling compound comprising a compound of formula I, wherein B is either a phosphoramidite group, an H-phosphonate, or a CPG.

Another embodiment of the current invention is a method of synthesizing an oligonucleotide comprising a compound of formula I, wherein the compound is a universal base according to the above definition, comprising the step of incorporation of a labeling compound during oligonucleotide synthesis.

Another embodiment of the current invention is a method of synthesizing an oligonucleotide comprising a compound of formula I, wherein the compound is a universal base according to the above definition, comprising the step of incorporation of a labeling compound during oligonucleotide synthesis, wherein said labeling compound contains a reactive group for coupling of a signal entity to said reactive group.

In a further embodiment the compound of formula I, incorporated into an oligonucleotide, comprises a signal entity.

In another embodiment of the current invention an oligonucleotide, comprising a compound of formula I, is used as a hybridization probe.

In still another embodiment of the current invention an oligonucleotide, comprising a compound of formula I, is used as a single labeled probe.

In another embodiment an oligonucleotide, comprising a compound of formula I, is used as a member of one pair of FRET hybridization probes.

In another embodiment an oligonucleotide, comprising a compound of formula I with two signal entities, is used as a TAQMAN probe or Molecular Beacon probe.

DETAILED DESCRIPTION OF THE INVENTION

Figure 1:
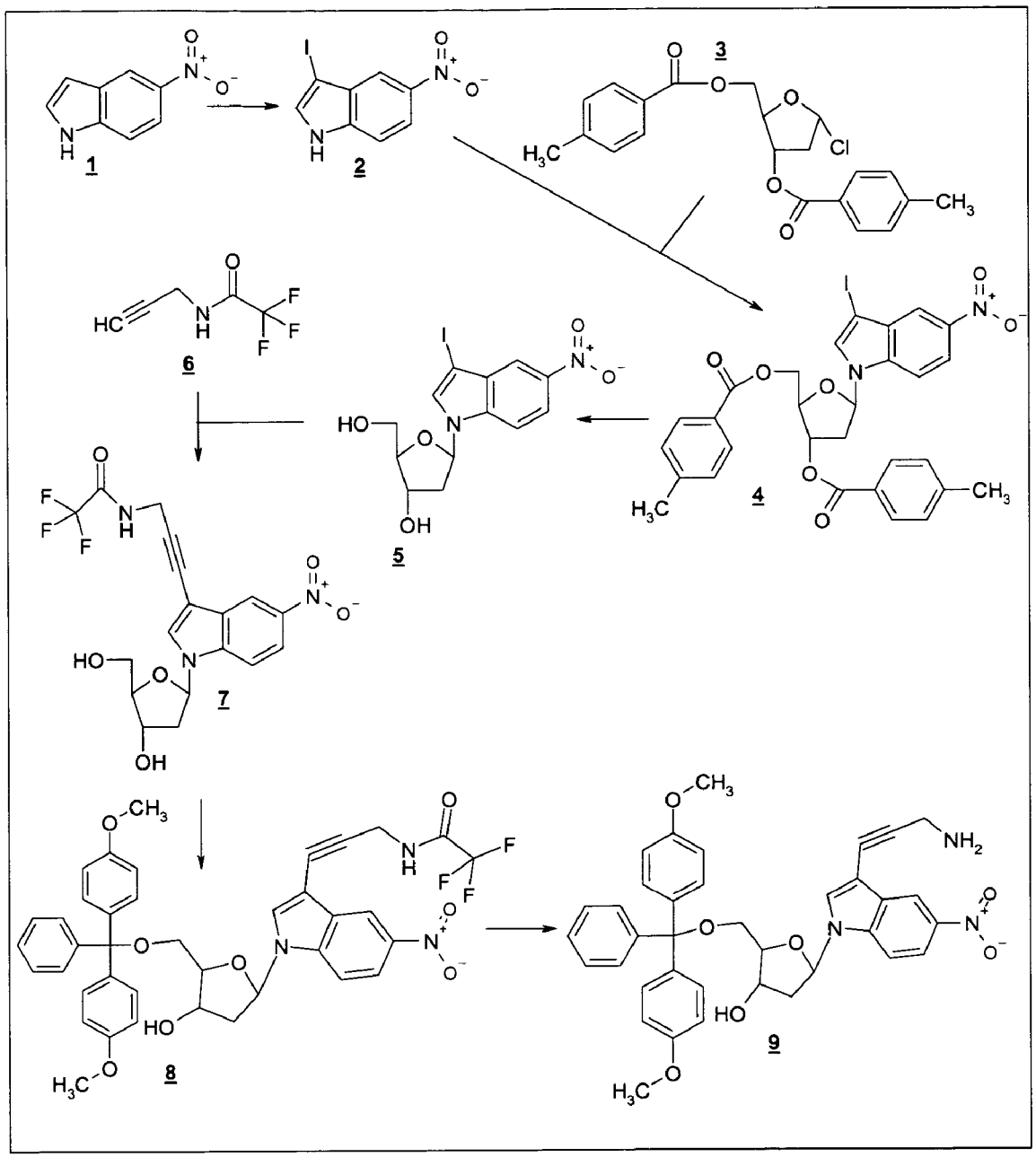
FIG. 1: Synthetic route to a nucleoside with reactive group (1=5-Nitro-1H-indole; 2=3-Iodo-5-nitro-1H-indole; 3=5-chloro-2-(4-methyl-benzoyloxymethyl)-3-(4-methyl-benzoyloxy)-tetrahydro-furan; 4=5-(3-Iodo-5-nitro-indol-1-yl)-2-(4-methyl-benzoyloxymethyl)-3-(4-methyl-benzoyloxy)-tetrahydro-furan; 5=2-Hydroxymethyl-5-(3-iodo-5-nitro-indol-1-yl)-tetrahydro-furan-3-ol; 6=2,2,2-Trifluoro-N-prop-2-ynyl-acetamide; 7=2,2,2-Trifluoro-N-{3-[1-(4-hydroxy-5-hydroxymethyl-tetrahydro-furan-2-yl)-5-nitro-1H-indol-3-yl]-prop-2-ynyl}-acetamide; 8=N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-2,2,2-trifluoro-acetamide; 9=5-[3-(3-Amino-prop-1-ynyl)-5-nitro-indol-1-yl]-2-[bis-(4-methoxy-phenyl)-phenyl-methoxymethyl]-tetrahydro-furan-3-ol)

The current invention is directed to a new, universally applicable, detectable compound for nucleic acid probes. The compound comprises a nucleoside with a modified universal base as nucleobase. This nucleoside shows improved synthetic and detection properties.

Within the scope of the present invention some of the terms used are defined as follows:

An "oligonucleotide" is a linear oligomer of natural or modified monomeric subunits and consists of a sequence composed of two or more monomeric subunits. These subunits are referred to as nucleotides. An oligonucleotide is optionally derived from natural sources, but is often synthesized chemically. It is of any size. The term "nucleotide" encompasses in connection with the present invention not only (deoxy)-oligo-ribonucleotides but also all back-bone modifications, as, e.g., methylphosphonates or phosphothioates, all sugar modifications, as, e.g., LNA, HNA, 2'-O-alkyl derivatives, and all base analogs, as, e.g., 7-deazapurines, as well as chimeras comprising different types of nucleic acids and analogues thereof.

An "oligonucleotide analogue" refers to a polymer with two or more monomeric subunits, wherein at least one of the monomers is not belonging to the group of natural nucleotides (A, T, C, G, and U). This non-natural nucleotide has some structural features in common with a naturally occurring nucleotide which allow it to interact with naturally occurring nucleotides.

The expressions "chain of nucleotides" or "chain of nucleotide residues" which are used interchangeably within this application refer to a polymer with two or more monomeric subunits, wherein these subunits comprise nucleotides and modified nucleotides as defined above. The "chain of nucleotides" is of any size, preferably of 5 to 70 monomeric subunits and more preferably of 10 to 40 monomeric subunits.

A "nucleoside" is a glycoside, normally a pentose glycoside, in which the aglycone, normally a heterocyclic base, is connected to a sugar moiety, normally a pentose.

A "protecting group" is any of the groups that have been designed to block one reactive site in a molecule during a chemical reaction that is carried out at another reactive site of this molecule. The protecting groups of the herein described synthesis can optionally be any of those described in Greene, et al., Protective Groups in Organic Chemistry, 2nd Ed., John Wiley & Sons, New York, N.Y., 1991.

A "labeled oligonucleotide" includes oligonucleotides having at least one label. The label may be a luorescent label but can also be of any other kind. The oligonucleotide may contain the label in various ways, including linked to a base of the oligonucleotide, or the dye may be used to replace a base as part of a "virtual nucleotide" structure. If there is more than one label attached, which could be of the same or of different types, than at least one of the labels is attached via the chemistry according to the invention. The other labels could be attached by other methods known in the art.

"Complementary" refers to nucleic acid sequences that form a base-paired structure with each other. "Complementary" refers in the case of oligonucleotides to the opposing strand and when discussing individual bases of an oligonucleotide, "complementary" refers to the position or base on the opposing strand. "Generally complementary" sequences are two nucleic acid sequences that have at least 80% homology due to the degeneracy of the genetic code. Thus, such sequences may have mismatches but have sufficient homology to form base-paired structures with each other.

A "signal entity" or "detectable label" is understood as substances that can be detected with the aid of analytical methods. These can for example be substances that can be detected with the aid of spectroscopy (visible-, UV-, IR- or mass spectroscopy); immunological assays or with the aid of NMR. In particular detectable labels are also understood to include fluorescent dyes such as fluoresceins, coumarines, oxazines, cyanines or rhodamines. Other labels included in this application are quencher molecules, haptenes, biotin, ruthenium-labels, spin-labels, mass tags and non-linear-optic labels.

One but not exclusive class of signal entities are fluorescent labels (fluorescent dyes) such as fluorescein and its derivatives (e.g., JOE, FAM, rhodamines, Alexa Fluor 488, Oregon Green dyes, erythrosines, eosins), fluorescein-cyanine conjugates (e.g., Big Dyes), derivatives of the bispyrromethene boron-difluoride dyes (e.g., BODIPY), cyanine monomers and dimers (e.g., TOTO, YOYO, TO-PRO, Cy3, Cy5, Cy5.5, Cy7, LCRed 705), immobilization to distinguishable supports or linkage to biomolecules (e.g., biotin). Some labels require protection if used directly in oligonucleotide synthesis, e.g., fluorescein is protected as bispivaloate.

The term "linker" represents a linear chain of atoms. This linear chain of atoms has a length of 1 to 20 atoms, preferred of 5 to 15 atoms, more preferred of 8 to 12 atoms. The linear chain may contain double and triple bonds. The linear chain may be substituted by alkyl-, alkenyl-, alkinyl-, aryl-groups as well as hetero-atoms. The linear chain may contain up to 20 heteroatoms. The linear chain may also contain a reactive moiety for further modification.

The term "double and triple bonds" means that said linear chain may contain one or more C—C double as well as triple bonds and C—N double bonds.

The term "substituted by alkyl-, alkenyl-, alkinyl-groups" comprises linear, branched and cyclic groups of $C_1$ to $C_6$ with or without heteroatoms.

The term "substituted by aryl-groups" comprises carbocyclic and heterocyclic groups with 4 to 10 ring atoms.

The term "substituted by hetero-atoms" comprises the substituents OH, =O, —O-alkyl, —O-alkenyl, —O-alkinyl, —O-aryl, —NH$_2$, —NH-alkyl, —NH-alkenyl, —NH-alkinyl, —NH-aryl, =NH, =N-alkyl, =N-alkenyl, =N-alkinyl, =N-aryl, —SH, —SO$_3$H, —S(O)$_2$NH$_2$, —Cl, —I, —Br, —F.

The term "may contain up to 20 heteroatoms" means that said linear chain is optionally interrupted up to five times or started or terminated by urea or urea derivatives, thiourea, —O—, —NH—, —N(CH$_3$)—, —S—, —S(O)$_2$—, —S(O)$_2$O—, —OS(O)$_2$—, —S(O)$_2$NH—, —NHS(O)$_2$—, —C(O)—, —OC(O), —C(O)O—, —NHC(O)— or —C(O)NH—.

Preferably said linear chain is optionally interrupted by —O—, —NH—, —NHC(O)— or —C(O)NH—.

The term "reactive group" comprises a moiety capable of attaching a detectable label. The reactive group is optionally protected by appropriate protective groups which are compatible with oligonucleotide synthesis. Said reactive group is selected from the group consisting of N-succinimidyl-oxycarbonyl, maleinimido, 4,6-dichloro-[1,3,5]triazin-2-amino-, N-benzotriazolyl-oxycarbonyl, N-phthalimidyl-oxycarbonyl, carboxylic acid, alkylcarbonyl-oxycarbonyl, arylcarbonyl-oxycarbonyl, alkoxycarbonyl, aryloxycarbonyl, imidate, imidazolide, p-aminobenzoyl, —C(O)Cl, —C(O)Br, —C(O)I, —SO$_2$Cl, —SO$_2$Br, —SO$_2$I, —NH$_2$, —N$_3$, —N=C=O, —N=C=S, —N$_2$+, —Cl, —Br, —I, —O—NH$_2$ or —N(R)—NH$_2$, whereby R is a $C_1$ to $C_6$ alkyl residue. The preferred reactive groups are N-succinimidyl-oxycarbonyl, maleinimido, carboxylic acid, alkylcarbonyl-oxycarbonyl, arylcarbonyl-oxycarbonyl, alkoxycarbonyl, aryloxycarbonyl, —NH$_2$, —N$_3$, —N=C=O, —N=C=S, —N$_2$+, —Cl, —Br, —I, —O—NH$_2$, OH, SH, or —N(CH$_3$)—NH$_2$. The —NH$_2$ group and its variants and analogs are the most preferred reactive groups and if used directly in oligonucleotide synthesis, this reactive group is protected with trifluoroacetyl. The reactive group is optionally attached via a linker.

The term "CPG" or "controlled pore glass" means available supports for the synthesis of oligonucleotides. The term CPG compromises synthesis supports which are used in standard oligonucleotide synthesis in order to attach signal entities, reactive groups, a nucleobase or analogs thereof or a phosphate to an oligonucleotide.

"Phosphoramidites" denotes molecules having a trivalent phosphorus atom which can be coupled to the 5'-terminal end of a nucleoside or nucleoside derivative. Thus phosphoramidites can be used to synthesize oligo-nucleotides. In addition to the (deoxy)-ribonucleotide phosphoramidites, which are used for chain extension, there are also phosphoramidites derivatized with a label which can be used in analogous processes to label the oligonucleotide during, at the beginning or at the end of oligonucleotide synthesis (Beaucage, S. L., Oligodeoxyribonucleotides Synthesis, In: Methods in Molecular Biology, Vol. 20, S.

Agrawal (ed.), Humana Press Inc., Totowa, N.J. (1993), pp. 33-61; Wojczewski, C., et al., Synlett 10 (1999) 1667-1678). In principle synthesis could also be performed in the 5' to 3' direction. This requires a phosphoramidate group on the 5' position and a protective group on the 3' position of the phosphoramidite.

Appropriate combinations of the above defined constituents according to chemical requirements and reasonable logic can be easily assembled by a person skilled in the art.

A "universal base" is a base analogue that does not discriminate between the five natural bases A, C, G, T and U. A "universal base" is characterized by a stable pairing with all natural bases after incorporation into double stranded nucleic acids, by being usable as part of a primer in nucleic acid synthesis and amplification, by incorporating all natural bases opposite it when copied by nucleic acid polymerases, by being a substrate for nucleic acid polymerases and by being clonable in vivo (Revankar, G. R., and Townsend, L. B., J. Heterocycl. Chem. 7 (1970) 1329-1332).

Universal bases are base analogues that can establish hydrogen bonding patterns similar to natural bases. Thus, these compounds are perfect substitutes for all natural bases A, C, G, T and U at the same time. In other "exchange"-systems rather a pi-stacking is established and not as in comparison with the natural bases a hydrogen bonding network. With universal bases as "exchange bases" such a network can be build and therefore only minor changes in, e.g., melting temperature of duplex DNA occur.

On the basis of this hydrogen bonding ability, universal bases can replace any natural base at any position in an oligo- and polynucleotide. This offers unique possibilities in view of nucleic acid techniques.

Universal bases comprise compounds like 5-nitroindole (Loakes, D., and Brown, D. M., Nucl. Acids Res. 22 (1994) 40394043), 3-nitropyrrole (Nichols, R., et al., Nature 369 (1994) 492493), 4-nitrobenzimidazole (Seela, F., et al., Helv. Chim. Acta 79 (1996) 488-498), indacenes and aza-derivatives thereof.

A universal base suitable as scaffold for the construction of universally applicable, labeled universal bases is 5-nitroindole. Duplexes formed with oligonucleotides containing this universal base display only small changes in, e.g., melting behavior or duplex formation.

To this day effective universal covalent labeling systems for oligo- and polynucleotides are only realized for the 3'- and 5'-terminal positions. In these positions dyes are incorporated during chemical oligonucleotide synthesis. For an internal labeling suitable labels, i.e. modified bases, have to be synthesized for all four nucleobases individually, e.g., TAMRA for uridine (see, e.g., Walton, T. A., et al., Bioconjugate Chem. 13 (2002) 1155-1158).

With the current invention universally applicable, labeling reagents are provided. These reagents can be easily incorporated during chemical and enzymatic synthesis at any position, i.e. at the 3'-position, the 5'-position, internally as substituent and as insertion (see, e.g., Verma, S., and Eckstein, F., Annu. Rev. Biochem. 67 (1998) 99-134).

The universally applicable, labeled 3-substituted 5-nitroindole universal base nucleoside has the general formula I:

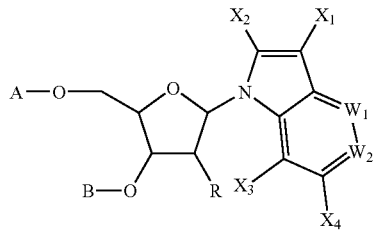

wherein A=H, phosphate, triphosphate, a protecting group, or a chain of nucleotide residues, B=H, a Phosphoramidite group, a H-phosphonate, a CPG, or a chain of nucleotide residues, R=H, OH, O-alkyl, O-alkenyl, or O-alkinyl, one of $W_1$, $W_2$=C—$NO_2$, and the other of $W_1$, $W_2$=CH or N, one of $X_1$, $X_2$, $X_3$, $X_4$ is either a reactive group or a protected reactive group or a linker with a reactive group or a linker with a protected reactive group or a signal entity or a protected signal entity or a linker with a signal entity or a linker with a protected signal entity, and the three others are H.

Compounds of formula I are permitting two alternative synthetic routes: (a) synthesis of oligonucleotides in the presence of a labeling group, and (b) synthesis of oligonucleotides in the presence of a reactive group for post synthesis modifications.

The compounds of formula I are accessible via chemical synthesis. An exemplary synthetic procedure for a compound of formula I with A=dimethoxy trityl (DMT), B=a phosphoramidite group, $X_2$ and $X_4$=hydrogen, $X_1$=reactive group with or without linker, $W_1$=CH, $W_2$=C—$NO_2$, is outline in FIG. 1 and Example 1. The starting point of the synthesis is 5-nitroindole which in the first step is substituted in the 3-position with iodine. Following the introduction of the iodine substituent in the 3-position is the assembly of the nucleoside basic structure by introducing a protected deoxypentose at the N-atom of the nitroindole. After deprotection of the hydroxyl groups a linker moiety bearing a protected reactive group is introduced. This linker moiety comprises mainly carbon, oxygen and nitrogen atoms. The role of the linker is on the one hand to provide a reactive group for the introduction of the detectable label and on the other hand to provide a flexible spacer allowing the detectable label to orient properly.

At this point the two synthetic routes diverge. If a label, that does not tolerate the conditions during oligonucleotide synthesis, shall be attached, the phosphoramidite residue is introduced at this stage. With this unlabelled nucleotide phosphoramidite bearing a protected reactive group the oligonucleotide synthesis is carried out and after synthesis and deprotection the detectable label is introduced in the final oligonucleotide.

If a label, that tolerates the conditions during oligonucleotide synthesis, shall be used the label is introduced prior to the formation of the phosphoramidite.

The phosphoramidite chemistry method is well known by any person skilled in the art. A 3'-phosphorous group of one nucleotide reacts with the 5'-hydroxyl moiety of another. The reaction proceeds from the 3'-to 5'-end, between each phosphor-amidite with a 5'-dimethoxytrityl protected monomer delivered in solution and the growing, 3' reactive oligonucleotide bound to an inert substrate.

Nascent oligonucleotides have the 5'-hydroxyl positions protected by dimethoxytrityl (DMT) groups, which have to be removed after each synthesis cycle in order to generate a reactive 5'-OH group of the nascent oligonucleotide chain. For product oligonucleotides, the DMT group can be removed during synthesis (TRITYL OFF) or left on (TRITYL ON) if reverse phase HPLC is the purification method of choice.

An example for the synthesis of a phosphoramidite bearing a reactive group is given in Example 1c, the synthesis of a labeled phosphoramidite is described in Example 1b. Other phosphoramidites bearing a reactive group or a label can be synthesized correspondingly.

These phosphoramidites can be used during oligonucleotide synthesis for providing oligonucleotides bearing a label or a reactive group at any position.

The synthesis of oligonucleotides is based on the method developed by Caruthers in the early eighties (Beaucage, S. L., and Caruthers, M. H., Tetrahed. Lett. 22 (1981) 1859-1862; McBride, L. J., and Caruthers, M. H., Tetrahed. Lett. 24 (1983) 245-248; for further reference see: Oligonucleotide Synthesis: A Practical Approach, Gait, ed., IRL Press, Oxford (1984); Kuijpers, W. H. A., et al., Nucleic Acids Research 18 (1990) 5197-5205; Dueholm, K. L., J. Org. Chem. 59 (1994) 5767-5773, Agrawal, S. (ed.) Methods in Molecular Biology, volume 20). In the first step the DMT protecting group is removed with a slightly acidic solution of, e.g., dichloroacetic acid or trichloroacetic acid in dichloromethane. For coupling the nucleoside which is to be coupled to the deprotected hydroxyl group is activated for the coupling reaction with tetrazole. The reaction product is afterwards oxidized, e.g., with an iodine/water/base mixture. The cycle is completed by capping hydroxyl groups that were not coupled during the coupling reaction.

An example for the synthesis of an oligonucleotide is given in Example 4.

The oligonucleotide synthesized with the labeled universal base according to the current invention at any position in the oligonucleotide are useful for many PCR applications. These pave the way for improved and new applications in nucleic acid chemistry.

In one embodiment, oligonucleotides containing an internal label according to the invention are used as hybridization probes. The internal label may be an integral part of any kind of hybridization probes, such as TAQMAN probes, Molecular Beacons, or may be an integral part of one or both members of a pair of FRET hybridization probes. Those hybridization probes according to the invention may be used for hybridization on blots, microtiter plates, microarrays, and, in particular, for real time PCR.

In one embodiment of the current invention the labeled universal base containing nucleotide is used in a hybridization probe as a member of one pair of FRET hybridization probes. This use is not limited to a single pair but can be expanded to the application in a FRET multiplex hybridization assay.

In one embodiment the hybridization probe containing one or more labeled universal base containing nitroindole nucleotide is as a TAQMAN probe or a Molecular Beacon probe, wherein in said probe two signal entities are present, wherein said two signal entities are fluorescent dyes.

In the three above mentioned hybridization probe formats the interaction of at least two signal entities is required. These pairs are either a fluorescent dye and a quencher or two fluorescent dyes.

In an embodiment, using a hybridization probe or a pair of FRET hybridization probes according to the invention, temperature dependence of hybridization is monitored, for example by means of performing a melting curve analysis.

Real time PCR melting curve analysis is usually performed after completion of the PCR-reaction. After an initial denaturation and cooling step, the temperature of the amplicon is constitutively increased, and fluorescence is detectable as long as the hybridization probe is bound to the target DNA. In case of the FRET hybridization probe format, both probes need to stay hybridized to the target nucleic acid in order to generate a fluorescent signal. At the melting temperature, the hybridization probes (in case of the FRET format: at least one member of said pair of hybridization probes) are released from their target, and the fluorescent signal is decreasing immediately down to the background level.

This decrease is monitored with an appropriate fluorescence versus temperature-time plot such that a first derivative value can be determined, at which the maximum of fluorescence decrease is observed.

One aspect of the present invention is based on the usage of differently labeled hybridization reagents, each reagent comprising a pair of FRET hybridization probes, comprising a pair of two fluorescent dyes which interact with each other on the principle of fluorescence resonance energy transfer (FRET).

More precisely, such a hybridization reagent is composed of two adjacently hybridizing oligonucleotides, appropriately labeled such that together they can act according to the FRET-hybprobe detection format as disclosed in WO 97/46707, WO 97/46712, and WO 97/46714.

In many cases, it is sufficient if the hybridization reagent consists of a single labeled oligonucleotide or in case of the FRET hybprobe format, of a pair of oligonucleotides acting together as a donor probe and an acceptor probe. Yet, in other cases there may exist many other sequence variants in the target sequences which need to be detected. Thus it may be impossible to detect the sequences of all members by just using just one pair of FRET oligonucleotide hybridization probes.

An important and significant method for the detection and mapping of, e.g., single nucleotide polymorphisms (SNPs), i.e. the variation of a single base in a polynucleotide sequence is the melting curve analysis. By heating double stranded polynucleotide molecules the hydrogen bond based interactions holding the strands together are reduced. At a specific temperature the two stands dissociate. This temperature is dependent on the length of the double stranded polynucleotide, the degree of GC content and the degree of complementarity between the stands. The temperature at which 50% of the double stranded polynucleotide becomes single stranded is termed melting temperature Tm.

This technique is especially important for the analysis of heteroduplexes formed between single stranded polynucleotide molecules and sequence-specific oligonucleotide probes. As already mentioned above the melting temperature is depending on the complementarity of the two single strands. This parameter is very sensitive so that actually one single base mismatch is detectable by a decrease of the melting temperature. That is, probe/polynucleotide heteroduplexes containing only a single mismatch are melting at a lower temperature than perfectly paired heteroduplexes. This demonstrates that even very small destabilization effects can be detected and quantified.

The basic principle behind this technique is labeled probes, especially fluorescently labeled sequence-specific oligonucleotide probes. The signal intensity and thus the sensitivity of the method is determined by the distance between the label and the mismatch to be detected. The closer the label to the mismatch the more intensive is the fluorescence signal and the change in the signal aroused by base mismatches.

A melting curve analysis comprises in general three steps: (i) in the first step a sequence-specific fluorescence labeled oligonucleotide probe is added to the PCR mixture, (ii) the second step comprises the amplification of the polynucleotide by PCR and (iii) in the third step the formed heteroduplexes between the single stranded target polynucleotide and the probe are slowly heated and the changes in fluorescence are recorded in dependency to the temperature which results in the recording of a melting curve.

With the subject of the current invention, a labeled base that can be incorporated at any position within an oligonucleotide probe, the expressiveness and significance of the melting curve analysis can be increased significantly. This is exemplified in Examples 3 and 5 as well as in FIG. 4.

Figure 4:
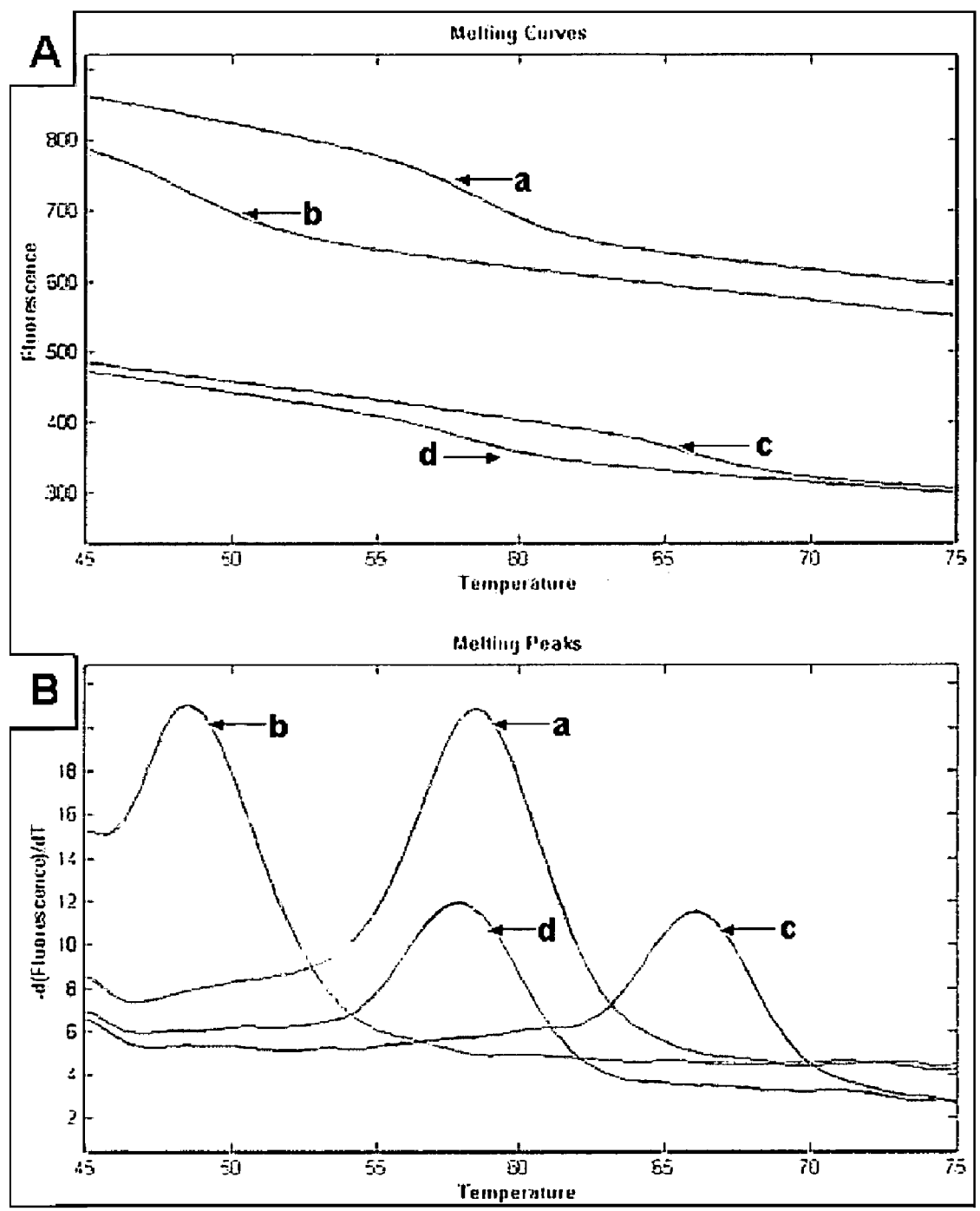
FIG. 4: Comparison of internally and terminally labeled detector oligonucleotide SLP 2 (SEQ ID NO: 5) versus reference (SEQ ID NO: 03).

In FIG. 4 the advantage of internal labeling in comparison to terminal labeling is outlined. In FIG. 4, e.g., a C/C and a T/T homozygous sample is analyzed. The melting curve is displayed in the lower part of the figure and the negative first derivative of the melting curve, i.e. the intensity of the change of the fluorescence signal, in the upper part of the figure. It is evident from these two graphs that an internally labeled probe provides a greater difference in the fluorescence signal and concomitantly a greater differential signal.

The results are summarized in the table below.

TABLE 1

|  | Area Tm1 | Area Tm2 |
| --- | --- | --- |
| T/T homozygous | | |
| internal label | 53 | — |
| terminal label | 25 | — |
| enhancement | 2.12 | — |
| C/C homozygous | | |
| internal label | — | 83 |
| terminal label | — | 42 |
| enhancement | — | 1.97 |

This experimental data emphasizes the advantages of the new universally applicable labeled base. With the internal labeling a signal intensity enhancement of approximately or more than 100% can be achieved. With this enhancement the overall sensitivity of the process is increased.

The signal enhancement is also important for real time PCR applications. In these applications the fluorescence signal emitted from heteroduplexes of amplified polynucleotide and labeled probe oligonucleotide is used for relative and absolute quantitation of the polynucleotide number and concentration. Among others determination of viral loadings or diagnosis of tumors as well as determination of gene expression are application areas of quantitative real-time PCR.

The examples, sequence listing, and figures are provided to aid the understanding of the present invention, the true scope of which is set forth in the appended claims. It is understood that modifications can be made in the procedures set forth without departing from the spirit of the invention.

DESCRIPTION OF THE SEQUENCES

SEQ ID NO: 01: PCR-primer sense for Genotyping of the MDR-1 C3435T Polymorphism
SEQ ID NO: 02: PCR-primer antisense for Genotyping of the MDR-1 C3435T Polymorphism
SEQ ID NO: 03: Single labeled detector probe for Genotyping of the MDR-1 C3435T Polymorphism
SEQ ID NO: 04: SLP 1
SEQ ID NO: 05: SLP 2

SPECIFIC EMBODIMENTS

Example 1a

Nitroindole Nucleoside

Preparation of 5-Nitroindole nucleoside a) 3-Iodo-5-nitro-indole

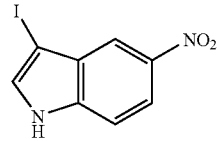

25.0 g (154.2 mmol) 5-nitroindole (Aldrich N1,760-2) and 21.7 g (386.7 mmol) potassium hydroxide (Ident. 1087347-001) were dissolved in 270 ml DMF. To this solution 39.5 g (155.6 mmol) iodine dissolved in 250 ml DMF were added drop wise during one hour. The resulting mixture was subsequently stirred for 1.0 h at room temperature. Afterwards the reaction mixture was poured on 2.5 l of sludge. The formed precipitate was collected by filtration and washed twice with water. The residue obtained was dried in a vacuum (yield: 43.0 g).

b) 5-chloro-2-(4-methyl-benzoyloxymethyl)-3-(4-methyl-benzoyloxy)-tetrahydro-furan

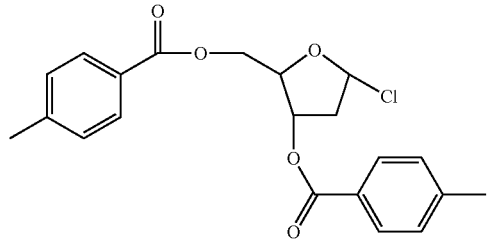

45.0 g (335.5 mmol) of 2-deoxy-D-ribose (Fluka 31170) were dissolved in 540 ml of anhydrous methanol (Ident. 0577286-001). To this solution a mixture of 90 ml methanol and 1.53 ml (21.5 mmol) acetyl chloride (Aldrich 40,279-6) were added drop wise at room temperature. The resulting mixture was stirred for an additional 15 min. at room temperature. After the addition of 18.0 g (214.3 mmol) sodium bicarbonate (Ident. 11270834-001) the resulting suspension was stirred for 15 min. After filtration of the suspension the solvent was removed by distillation. To the oily brown residue 75 ml of anhydrous pyridine were added and subsequently the solvent was removed in a vacuum on a rotary evaporator. This procedure was repeated three times. The remaining residue was dissolved in 270 ml anhydrous pyridine and cooled to 0° C. At this temperature 99 ml (748.6 mmol) of p-toluoyl chloride (Aldrich 10,663-1) were added drop wise over a period of 90 minutes. Afterwards the reaction mixture was stirred for an additional 12 hours at room temperature. The suspension was poured on 1.5 l sludge and the aqueous phase was extracted three times each with 600 ml dichloromethane (Ident. 11270834-001). The combined organic phases were washed twice each with 600 ml water, three times each with 600 ml 2 M hydrochloride acid, twice each with 600 ml saturated sodium bicarbonate solution and twice each with 600 ml water. Afterwards the separated organic phase was dried over sodium sulfate and evaporated to dryness in a vacuum on a rotary evaporator. The oily residue was dissolved in 180 ml glacial acetic acid and 280 ml of a mixture of 228 ml glacial acetic acid, 45.9 ml (646 mmol) acetyl chloride and 11.3 ml water were added with stirring and with cooling on ice. The pulp was removed by filtration and washed twice each with 200 ml of ice cold diethyl ether. The residue was dried over potassium hydroxide in a vacuum. (yield: 96.3 g).

c) 5-(3-Iodo-5-nitro-indol-1-yl)-2-(4-methyl-benzoyloxymethyl)-3-(4-methyl-benzoyloxy)-tetrahydro-furan

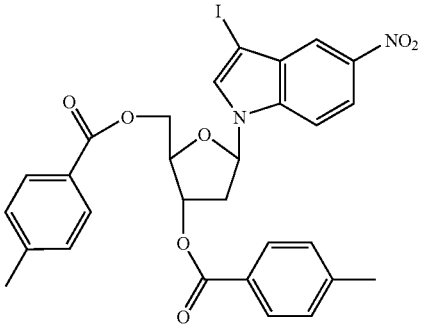

To a suspension of 1.0 g (3.5 mmol) 3-iodo-5-nitroindole in 15 ml acetonitrile were added 0.16 g (6.7 mmol) sodium hydride (Aldrich 223441-SOG). The stirring was continued and the suspension turned red. After 15 min. 2.02 g (5.2 mmol)

5-chloro-2-(4-methyl-benzoyloxymethyl)-3-(4-methyl-benzoyloxy)-tetrahydro-furan were added in small portions and the stirring was continued for another 60 minutes at room temperature. The precipitate was removed by filtration and washed once with acetonitrile. The combined yellow filtrates were concentrated until a product precipitated. For complete precipitation of the product 50 ml ethanol were added. The yellow precipitate was removed by filtration und washed with ethanol. The residuum was dried over phosphorus pentoxide and potassium hydroxide in a vacuum (yield: 1.9 g).

d) 2-Hydroxymethyl-5-(3-iodo-5-nitro-indol-1-yl)-tetrahydro-furan-3-ol

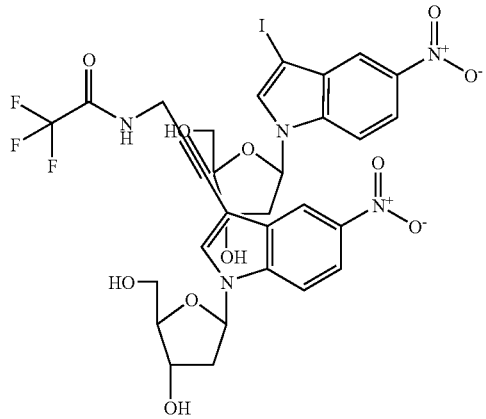

To a suspension of 12 g (18.7 mmol) of the indole derivative 5-(3-Iodo-5-nitro-indol-1-yl)-2-(4-methyl-benzoyloxymethyl)-3-(4-methyl-benzoyloxy)-tetrahydro-furan in 600 ml ethanol 4.2 g (37.5 mmol) potassium tert-butylate were added. The suspension was stirred for 12 hours at room temperature. The resulting yellow solution was chromatographed on a silica gel column (Silica gel 60, Merck, 230×100 mm) with a gradient starting at 100% dichloromethane to 85% dichloromethane: 15% methanol (yield: 6.6 g).

e) 2,2,2-Trifluoro-N-prop-2-ynyl-acetamide

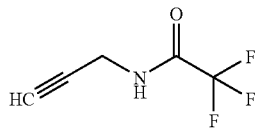

To 15 g (272.3 mmol) propargylamine in 275 ml anhydrous methanol 36.6 g (285.9 mmol) methyl trifluoroacetate were added with cooling. The resulting reaction mixture was stirred for an additional four hours at room temperature. Afterwards the solvent was removed by distillation at reduced pressure. The residue was dissolved in 300 ml trichloromethane and extracted four times, twice each with 300 ml of a saturated sodium bicarbonate solution and twice each with 300 ml water. The separated organic phase was dried over magnesium sulfate, filtrated and the solvent was removed by distillation (yield: 23.3 g).

f) 2,2,2-Trifluoro-N-{3-[1-(4-hydroxy-5-hydroxymethyl-tetrahydro-furan-2-yl)-5-nitro-1H-indol-3-yl]-prop-2-ynyl}-acetamide 19.8 g (48.99 mmol) of 2-hydroxymethyl-5-(3-iodo-5-nitro-indol-1-yl)-tetrahydro-furan-3-ol were placed in a preheated flask in an argon atmosphere and dissolved in 200 ml anhydrous tetrahydrofuran. 27.2 ml (196.2 mmol) of triethylamine (Merck, 8.08352.1000), 1.87 g (9.82 mmol) of copper (I) iodide (Merck, 8.18311.0100) and 5.66 g (4.89 mmol) of tetrakis(triphenylphosphine)palladium(0) (Merck, 8.14761.005) were added. After 5 minutes at room temperature 19.8 ml of 2,2,2-trifluor-N-propyl-2-ynyl-acetamide were added and it was stirred for a further 45 minutes. The solvent was removed by distillation. The residue was chromatographed on a silica gel column (Silica gel 60, Merck, 400×70 mm) with a gradient starting at 100% dichloromethane to 95% dichloromethane with 5% methanol (yield: 17.06 g).

g) N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-2,2,2-trifluoro-acetamide

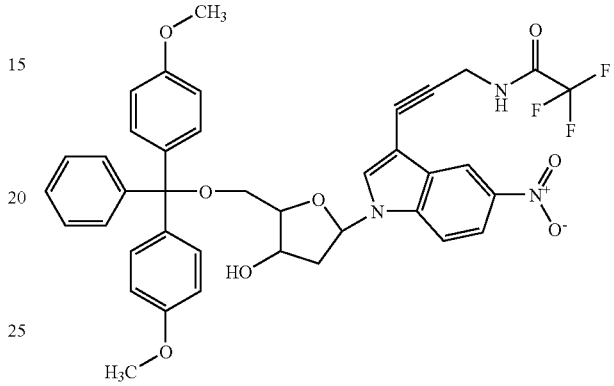

8.4 g (19.7 mmol) 2,2,2-Trifluoro-N-{3-[1-(4-hydroxy-5-hydroxymethyl-tetrahydro-furan-2-nitro-1H-indol-3-yl]-prop-2-ynyl}-acetamide and 7.8 g (21.8 mmol) of 4,4'-dimethoxytriphenylmethyl chloride (Aldrich 10,001-3) were placed in an argon atmosphere in a flame dried 250 ml flask. The substances were dissolved in 90 ml anhydrous pyridine (Aldrich 27,097-0) and stirred for one hour with exclusion of humidity. The solvent was removed in a vacuum on a rotary evaporator. The residue was chromatographed on a silica gel column (Silica gel 60, Merck, 185×85 mm) with a gradient starting with a solvent mixture of 2-butanone:hexane 3:4 (v/v) with 0.1 vol % triethylamine to a solvent mixture of 2-butanone:hexane 1:1 (v/v) with 0.1 vol % triethylamine. The solvent was removed after addition of 50 ml toluene in a vacuum on a rotary evaporator with a water bath temperature of 38° C. (yield: 11.1 g).

h) 5-[3-(3-Amino-prop-1-ynyl)-5-nitro-indol-1-yl]-2-[bis-(4-methoxy-phenyl)-phenyl-methoxymethyl]-tetrahydro-furan-3-ol

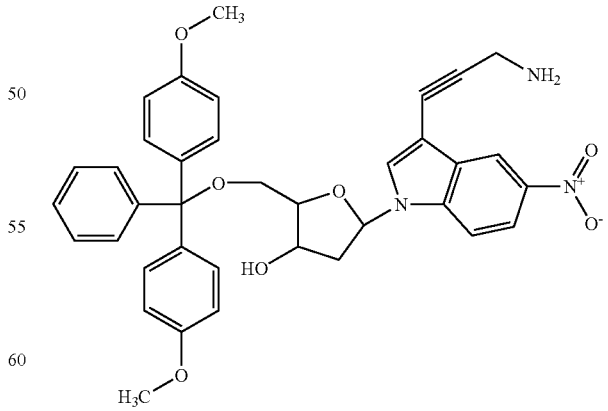

11.0 g (15 mmol) N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-2,2,2-trifluoro-acetamide were dissolved in 260 ml 7N ammonia solution in methanol (Aldrich, 499145). The solution was maintained at 8° C. for 16 h. The solvent was removed in a vacuum on a rotary evaporator (water bath 38° C.). The residue was chromatographed on a silica gel column (Silica gel 60, Merck, 280×85 mm) with a solvent mixture of ethyl acetate:methanol:toluene 1:1:4 (v/v/v) with 0.2 vol % triethylamine (yield: 6.1 g).

Example 1b

Phosphoramidite for Oligonucleotide Synthesis Labeled with Fluorescein

Phosphoramidite for Simple Probe Labeling with Fluorescein a) Carboxyfluorescein-di-pivaloyate

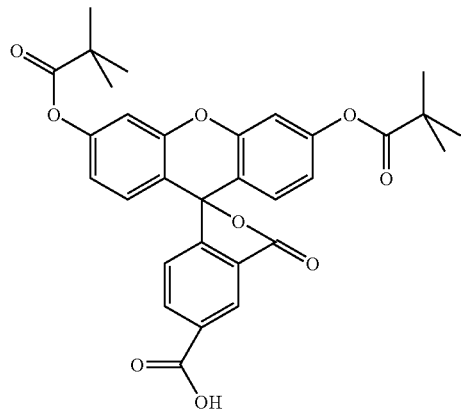

9.5 g (25 mmol) 5'-carboxyfluorescein were dissolved in 500 ml dichloromethane. 18.7 ml (125 mmol) 1,8-diazabicyclo[5.4.0]undec-7-ene (DBU, Aldrich 13,900-9), 12.75 ml (61.5 mmol) pivalic acid anhydride (Merck, 8.01302.0100) and 0.5 g (4 mmol) 4-dimethylaminopyridine (DMAP, Fluka, 39405) were added and dissolved. The resulting mixture was refluxed for 2.5 hours. Afterwards the reaction mixture was cooled to room temperature and extracted twice with each 300 ml citric acid 10% (w/w) and once with 200 ml of a saturated sodium chloride solution. The separated organic phase was dried over sodium sulfate for 10 minutes, filtrated and subsequently the solvent was removed in a vacuum on a rotary evaporator. The residue was chromatographed on a silica gel column (Silica gel 60, Merck, 180×95 mm) with a solvent mixture of 90:10 (v/v) ethyl acetate:hexane (yield: 10.6 g).

b) NHS-ester

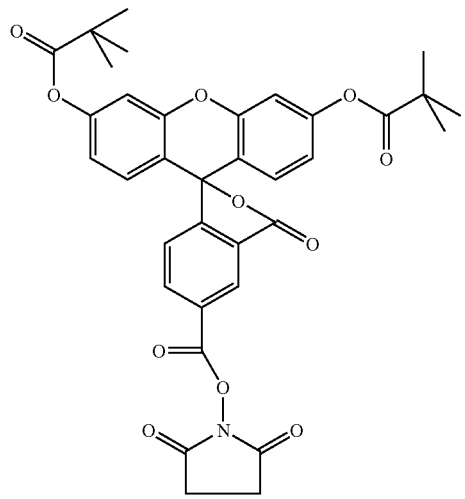

6.5 g (111.9 mmol) of the carboxyfluorescein-di-pivaloyate and 1.55 g (13.1 mmol) N-hydroxysuccinimide (NHS, Fluka, 56480) were dissolved in 220 ml dichloromethane. Subsequently 3.0 g (14.4 mmol) of N,N'-dicyclohexylcarbodiimide (DCC, Fluka, 36650) were added. The reaction mixture was stirred for three hours with the exclusion of humidity. Afterwards the solvent was removed in a vacuum on a rotary evaporator with 35° C. water bath temperature. The residue was suspended in 370 ml ethyl acetate. The undissolved DCH was removed by filtration. The filtrate was extracted twice with each 150 ml citric acid 10% (w/w) and once with 150 ml of a saturated sodium chloride solution. The separated organic phase was dried over sodium sulfate for 10 minutes, filtrated and subsequently the solvent was removed in a vacuum on a rotary evaporator (bath temperature 35° C.).

c) Substitution of the NHS-Ester

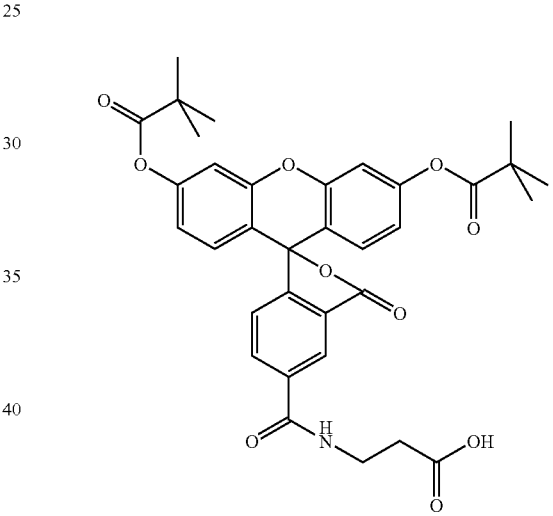

To the solution of the NHS-ester of the previous step in 130 ml dioxane 1.6 g (17.9 mmol) beta-alanine (Merck, 1008) dissolved in 40 ml water was added drop wise. After finishing the addition 30 ml of a saturated sodium bicarbonate solution were added. The reaction solution turned yellow-orange. Stirring was continued for another 1.5 hours at room temperature. For work up 370 ml ethyl acetate were added and the resulting mixture was extracted twice with each 200 ml citric acid 10% (w/w) and once with 150 ml of a saturated sodium chloride solution. The separated organic phase was dried over sodium sulfate for 10 minutes, filtrated and subsequently the solvent was removed in a vacuum on a rotary evaporator (bath temperature 35° C.). The residue was digested with 100 ml hexane, the solvent removed by filtration, washed with hexane and the residue was dried in a vacuum over night.

d) Coupling of Dye to Nitroindole Base

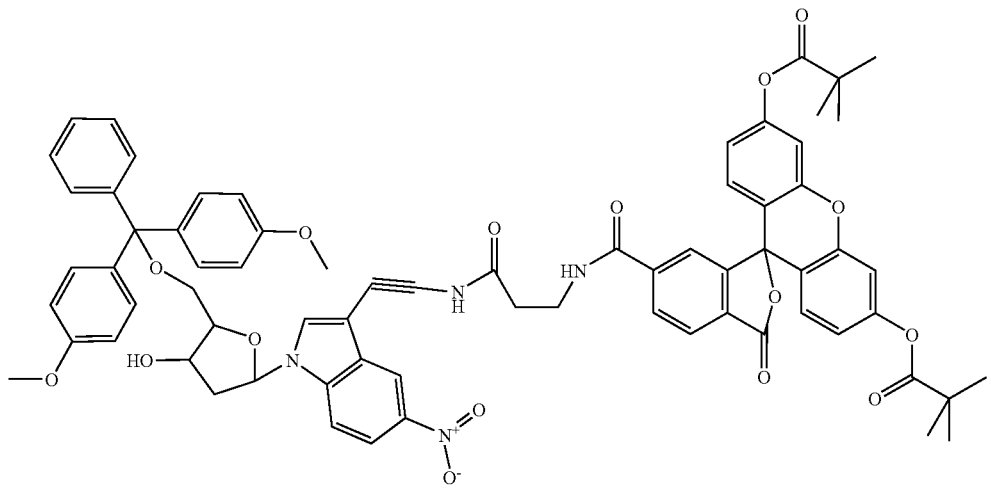

6.2 g of the acid of the previous step, 1.3 g NHS and 2.5 g DCC were dissolved in 200 ml dry dichloromethane with the exclusion of humidity and stirred for two hours. Afterwards the reaction mixture was filtered with a plaited paper filter and the filtrate was concentrated in a vacuum on a rotary evaporator. The residue was suspended in 400 ml ethyl acetate, undissolved DCH was removed by filtration. The filtrate was extracted twice with each 150 ml citric acid 10% (w/w) and once with 150 ml of a saturated sodium chloride solution. The separated organic phase was dried over sodium sulfate, filtrated and subsequently the solvent was removed in a vacuum on a rotary evaporator (bath temperature 35° C.). The residue was dried over calcium chloride in a vacuum for one hour. The dried residue was dissolved in 200 ml dichloromethane and 6.33 g (10 mmol) N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-amine and 4.2 ml (30 mmol) of triethylamine were added. The mixture was stirred with the exclusion of humidity for 75 minutes at room temperature. Afterwards the solvent was removed in a vacuum on a rotary evaporator.

The residue was chromatographed on a silica gel column (Silica gel 60, Merck, 310×85 mm) with a solvent mixture of toluene:ethyl acetate:methanol 4:3:1 (v/v/v) with 0.2 vol % triethylamine (yield: 8.1 g).

e) Nitroindole Phosphoramidite with Fluorescence Label 2.36 g (2.0 mmol) of the previously prepared nucleoside, 30 ml dichloromethane (Merck, 1.06051.0500), 1.044 ml (6.1 mmol) of N-ethyldiisopropylamin (Fluka, 03440) and 0.566 ml (2.5 mmol) of chloro-2-cyanoethoxydiisopropylamino phosphane monochloride (Proligo, M 901005/222352) were mixed in an argon atmosphere. Subsequently the reaction mixture was stirred for 40 minutes and was directly chromatographed on silica gel (Merck, 1.09385.9025, 120×50 mm, solvent 1 liter dichloromethane with 0.2 vol % triethylamine, followed by 0.5 liter dichloromethane:acetone 94:6 (v/v) with 0.2 vol % triethylamine, followed by 1.0 liter dichloromethane:acetone 90:10 (v/v) with 0.2 vol % triethylamine). The fractions containing the product were combined and subsequently the solvent was removed in a vacuum on a rotary evaporator (bath temperature 35° C.). To the residue was added a small volume of dichloromethane. The solvent was removed in a vacuum and the residue was dried for three hours at room temperature in a vacuum (yield: 1.5 g).

Example 1c)

Phosphoramidite for Oligonucleotide Synthesis Bearing a Reactive Group

Preparation of Phosphoramidite for Post-Synthesis Labeling
a) N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-2,2,2-trifluoro-acetamide

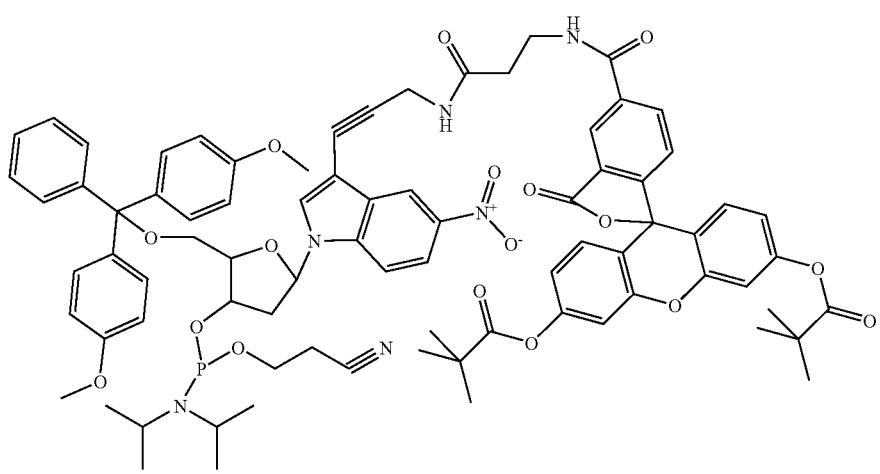

6.9 g (16.8 mmol) 2,2,2-Trifluoro-N-(3-(1-(4-hydroxy-5-hydroxymethyl-tetrahydro-furan-2-yl)-5-nitro-1H-indol-3-yl)-prop-2-inyl)-acetamide and 6.33 g (17.8 mmol) 4,4'-dimethoxytriphenylmethylchloride (Aldrich 10,001-3) were dissolved in 70 ml pyridine (Aldrich 27,097-0) and stirred for 16 hours with the exclusion of humidity. The solvent was removed in a vacuum on a rotary evaporator (bath temperature 38° C.). The resulting dark brown oil was chromatographed on a silica gel column (Silica gel 60, Merck, 260×85 mm) with a solvent mixture of toluene:ethyl acetate:methanol 4:1:1 (v/v/v) with 0.3 vol % triethylamine. The solvent of the combined product containing fractions was removed in a vacuum on a rotary evaporator. The residue was dissolved in dioxan and lyophilized (yield: 7.67 g).

b) Diisopropyl-phosphoramidous acid 2-[bis-(4-methoxy-phenyl)-phenyl-methoxymethyl]-5-{5-nitro-3-[3-(2,2,2-trifluoro-acetylamino)-prop-1-ynyl]-indol-1-yl}-tetrahydro-furan-3-yl ester 2-cyano-ethyl ester 1.5 g (2 mmol) N-[3-(1-{5-[Bis-(4-methoxy-phenyl)-phenyl-methoxymethyl]-4-hydroxy-tetrahydro-furan-2-yl}-5-nitro-5-1H-indol-3-yl)-prop-2-ynyl]-2,2,2-trifloro-acetamide, 1.04 ml (6 mmol) N-ethyl-diisopropyl amine (Fluka 03440) and 0.9 ml (4 mmol) Chloro-2-cyanoethoxydiisopropylaminophosphan-monochloride were sequentially dissolved in 20 ml anhydrous dichloromethane (Fluka 6749) in a dried reaction flask under an argon atmosphere. The sealed reaction vessel was stirred for 45 minutes. The reaction mixture was afterwards directly chromatographed on a silica gel column (Silica gel 60, Merck, 200×60 mm) with a solvent mixture of dichloromethane:acetone 30:2.5 (v/v) with 0.1 vol % triethylamine. The solvent of the combined product containing fractions was removed in a vacuum on a rotary evaporator (bath temperature 28-30° C.). The resulting oil was dissolved in 15 ml dichloromethane. This solution was added in drops to 250 ml n-hexane with strong agitation. The precipitate was separated by centrifugation (4 min. at 4000 U/min) and washed once with hexane. The residue was dissolved in 20 ml dichloromethane and apportioned to glass bottles. The solvent was removed in a stream of nitrogen (yield: 1.2 g).

Example 2

CPG with Fluorescein

CPG with Fluorescein—Preparation of 6'-carboxyfluorescein-nitroindole-CPG a) N-[3-(1-{5-[Bis-(4-methoxy-phenyl)-phenyl-methoxymethyl]-4-hydroxy-tetrahydro-furan-2-yl}-nitro-1H-indol-3-yl)-prop-2-ynyl]-2,2,2-trifluoro-acetamide In a 50 ml flask flame dried in a nitrogen atmosphere 0.84 g (1.97 mmol) of 2,2,2-trifluoro-N-(3-(1-(4-hydroxy-5-hydroxymethyl-tetrahydrofuran-2-yl)-5-nitro-1H-indol-3-yl)-prop-2-ynyl)-2,2,2-trifluoroacetamide, 9.0 ml pyridine (Aldrich 27,097-0) and 0.78 g (2.18 mmol) 4,4'-dimethoxytriphenylmethylchloride (Aldrich 10,001-3) were mixed and stirred for one hour in the absence of humidity. The solvent (pyridine) was removed in a vacuum on a rotary evaporator. The resulting brown residue was chromatographed on silica gel (Merck, 1.09385.9025, 210×35 mm, solvent gradient, start: methylethylketone:hexane 3:4 (v/v) with 0.1 vol % triethylamine, end: methylethylketone:hexane 1:1 (v/v) with 0.1 vol % triethylamine). The fractions containing the product (TLC) were combined and 30 ml toluene were added. Subsequently the solvent was removed in a vacuum on a rotary evaporator (bath temperature 38° C., yield: 1.11 g).

b) N-[3-(1-{5-[Bis-(4-methoxy-phenyl)-phenyl-methoxymethyl]-4-hydroxy-tetrahydro-furan-2-yl}-nitro-1H-indol-3-yl)-prop-2-ynyl]-amine 1.10 g (1.5 mmol) of N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-2,2,2-trifluoro-acetamide were dissolved in 26 ml of a 7N ammonia solution in methanol (Aldrich 499145). The sealed reaction vessel was stirred at 8° C. over night. The solvent is removed in a vacuum on a rotary evaporator (bath temperature 38° C.). The residue was chromatographed on silica gel (Merck, 1.09385.9025, 280×35 mm, solvent ethyl acetate/methanol/toluene 1:1:4 (v/v/v) with 0.2 vol % triethylamine). The fractions containing the product were combined and subsequently the solvent was removed in a vacuum on a rotary evaporator (yield: 0.61 g).

c) Carboxyfluorescein-dye 9.5 g (25 mmol) 6'-carboxyfluorescein were dissolved in 500 ml dichloromethane. 18.7 ml (125 mmol) 1,8-diazabicyclo[5.4.0]undec-7-ene (DBU, Aldrich 13,900-9), 12.75 ml (61.5 mmol) pivalic acid anhydride (Merck, 8.01302.0100) and 0.5 g (4 mmol) 4-dimethylaminopyridine (DMAP, Fluka, 39405) were added and dissolved. The resulting mixture was refluxed for 2.5 hours (if the 6'-carboxyfluorescein does not dissolve completely, 20 ml anhydrous N,N'-dimethylformamide may be added). Afterwards the reaction mixture was cooled to room temperature and extracted twice with each 300 ml citric acid 10% (w/w) and once with 200 ml of a saturated sodium chloride solution. The separated organic phase was dried over sodium sulfate for 10 minutes, filtrated and subsequently the solvent was removed in a vacuum on a rotary evaporator. The residue was chromatographed on a silica gel column (Silica gel 60, Merck, 180×95 mm) with a solvent mixture of 90:10 (v/v) ethyl acetate:hexane (yield: 10.6 g).

d) NHS-esterformation and Fluorescence Labeling of Nitroindole Base 5.5 g (10 mmol) of the protected fluorescence dye prepared in the previous step, 1.3 g (11 mmol) NHS (Fluka 56480) and 2.5 g (12 mmol) DCC (Fluka 36650) were dissolved in 200 ml anhydrous dichloromethane under exclusion of humidity. The reaction mixture was stirred for two hours at room temperature. Afterwards the reaction mixture was filtered with a plaited paper filter and the filtrate was concentrated in a vacuum on a rotary evaporator. The residue was suspended in 400 ml ethyl acetate, undissolved DCH was removed by filtration. The filtrate was extracted twice with each 150 ml citric acid 10% (w/w) and once with 150 ml of a saturated sodium chloride solution. The separated organic phase was dried over sodium sulfate, filtrated and subsequently the solvent was removed in a vacuum on a rotary evaporator (bath temperature 35° C.). The residue was dried over calcium chloride in a vacuum for one hour. The dried residue was dissolved in 200 ml dichloromethane. 6.33 g (10 mmol) N-[3-(1-{5-[Bis-(4-methoxy-phenyl)-phenyl-methoxymethyl]-4-hydroxy-tetrahydro-furan-2-yl}-5-nitro-1H-indol-3-yl)-prop-2-ynyl]-amine and 4.2 ml (30 mmol) of triethylamine were added. The mixture was stirred with the exclusion of humidity for 75 minutes at room temperature. Afterwards the solvent and the triethylamine were removed in a vacuum on a rotary evaporator. The residue was chromatographed on a silica gel column (Silica gel 60, Merck, 310×85 mm) with a solvent mixture of toluene:ethyl acetate:methanol 4:3:1 (v/v/v) with 0.2 vol % triethylamine (yield: 7.55 g).

e) Introduction of Linker Moiety

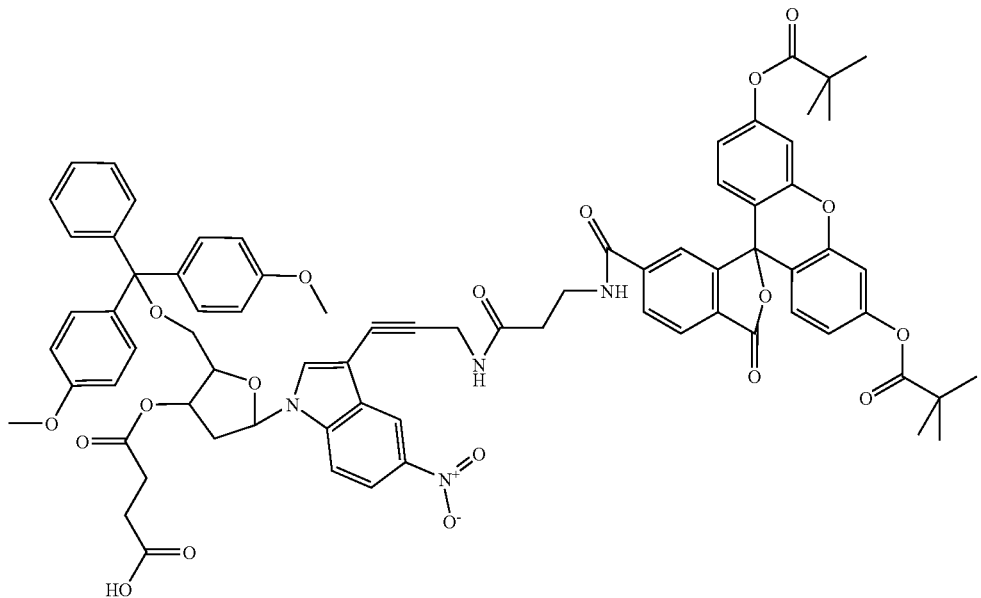

6.1 g (5 mmol) of the substance prepared in the previous step, 1.6 g succinic anhydride (Fluka 14089) and 123 mg (1 mmol) 4-dimethylaminopyridine (DMAP, 39405) were mixed in an argon atmosphere. The substances were dissolved in 100 ml anhydrous pyridine (Aldrich 27,097-0). The sealed reaction vessel was stirred over night. The pyridine was removed in a vacuum on a rotary evaporator. The resulting oil was chromatographed on a silica gel column (Silica gel 60, Merck, 320×60 mm) with a solvent mixture of toluene: ethyl acetate:methanol 4:1:1 (v/v/v) with 0.2 vol % triethylamine. The solvent of the combined product containing fractions was removed in a vacuum on a rotary evaporator. The residue was dissolved in dioxan and lyophilized (yield: 2.5 g).

f) Coupling to CPG

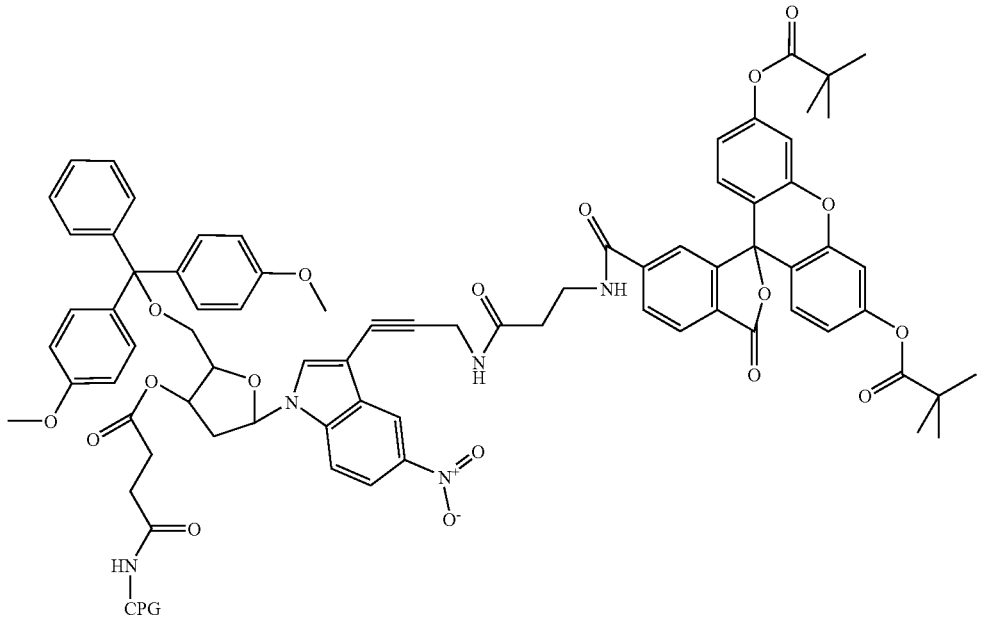

1.75 g (1.38 mmol) of the substance prepared in the previous step, 55 ml N,N'-dimethylformamide (DMF), 30 ml pyridine (Aldrich 27,097-0), 150 mg DMAP and 1.4 g N-(3-dimethylamiopropyl)-N'-ethylcarbodiimide hydrochloric acid salt (EDC, Fluka 03450) were mixed. Subsequently 19.4 g LCA-CPG are added and the mixture was shook over night in the sealed reaction vessel. Afterwards the reaction mixture was filtered over a D4 frit. The filter cake was washed consecutively with 200 ml DMF, 200 ml THF and 200 ml diethyl ether. The filter cake was suspended in 100 ml anhydrous pyridine (Aldrich 27,097-0). 25 ml acetic anhydride (Aldrich 11,004-3) were added. The reaction mixture was shaken at medium speed for 90 minutes and subsequently filtered over a D3 frit. The filter cake was washed subsequently with 300 ml THF and 200 ml diethyl ether. The support was dried in a desiccator in a vacuum for 4 hours. Yield: 16 g CPG with a loading of 36 lmoug. This CPG could be used for 3'-labeling of oligonucleotides.

Example 3

Genotyping of the MDR-1 C3435T polymorphism using a 5'-fluorescence-Dye Labeled Oligonucleotide To demonstrate the validity of the invention, genotyping of the MDR-1 C3435T single nucleotide polymorphism was chosen as test system and reference method. As detector probe an oligonucleotide carrying a terminal fluorescent-dye label was used for melting curve analysis (see also, e.g., WO 02/14555). Results are displayed in FIG. 2.

a) PCR

Genomic DNA was isolated from anonymous human blood samples using the MagNA Pure LC Instrument together with the MagNA Pure LC Total Nucleic Acid Isolation Kit according to the manufacturer's instructions (Roche Applied Science, Article No. 3003990). For amplification of genomic DNA the LightTyper 384 PCR Kit (Roche Applied Science, Article No. 03707695001) was used on a standard thermal cycler (GeneAmp PCR System 9700, ABI). A typical PCR assay consisted of 10 ng genomic DNA, 1× reaction buffer, 3.0 mM magnesium chloride and 1 unit of FastStart Taq DNA polymerase. Asymmetric PCR conditions were used to gain an excess of single stranded target molecules preferential for binding of the Fluorescence-dye labeled detector oligonucleotide. PCR primers were 1.0 μM (excess primer) and 0.2 μM (limiting primer), the detector oligonucleotide was used at 0.2 μM final concentration. PCR was carried out in 384 white-well microtiter plates (ABgene, UK) in a total reaction volume of 10 μl. Reaction mixes were overlaid with 10 μl of light mineral oil (Sigma-Aldrich, Germany). The PCR protocol consisted of an initial denaturation step at 94° C. for 10 min, followed by 40 cycles of amplification at 94° C. for 15 s, 58° C. for 15 s and 72° C. for 15 s. Samples were immediately cooled at 40° C. for 30s after a final denaturation at 94° C. for 30 s.

b) Fluorescent Melting Curve Analysis

The cooled plate was transferred to a LightTyper 384 Instrument (Roche Applied Science, Article No. 03357414001). For melting curve analysis samples were slowly heated (0.1° C./s) from 45° C. to 80° C. During heating, fluorescence emission of the dye-labeled detector oligonucleotide was continuously monitored. The Fluorescence dye was excited in the LightTyper instrument at 470 nm whereas Fluorescence emission was detected at 530 nm using an optical filter (510 nm long pass).

Sequences of PCR Primers and Detector-Probe:

PCR-primer sense (SEQ ID NO: 01): 5'-d(gatctgtgaactct-tgttttca)-3'

PCR-primer antisense (SEQ ID NO: 02): 5'-d(tttgaa-gagagacttacattaggc)-3'

Single labeled detector probe (SEQ ID NO: 03): 5'-FAM-n-d(tcacaggaagagatcgtgaggg)-p-3' (FAM: 6-carboxyfluores-cein, n: 1-(2-deoxy-beta-D-ribofuranosyl)-5-nitroindole, p: phosphate)

Figure 2:
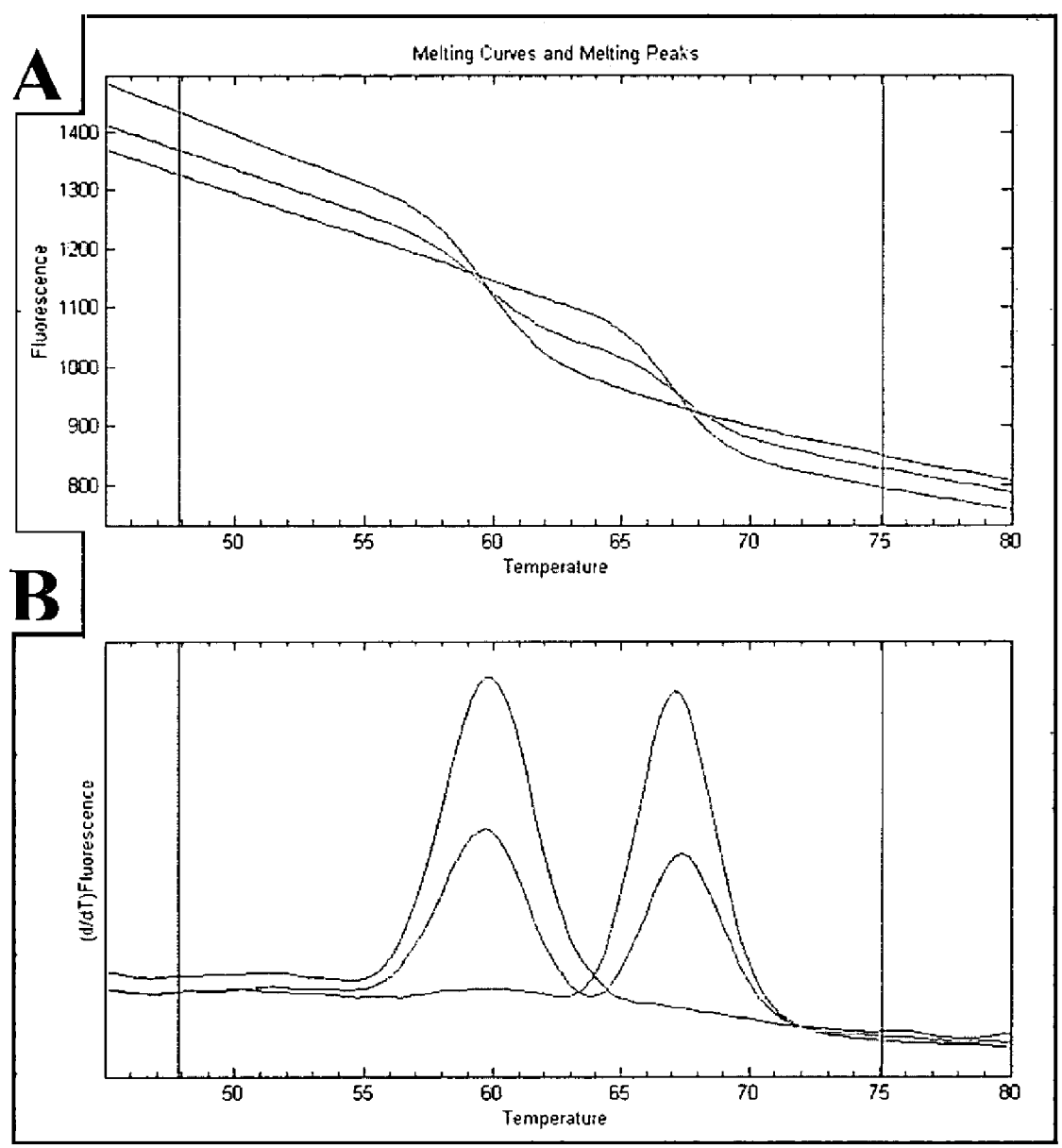
FIG. 2: Fluorescent melting curve analysis using a 5'-FAM-labeled detector oligonucleotide (SEQ ID NO: 03) reference.

In FIG. 2 melting curves (A) and melting peaks (B) are illustrated for each possible genotype of the MDR1 C3435T polymorphism. One melting peak was detected for each homozygous variant (C/C or T/T) whereas the heterozygous variant was characterized by 2 peaks (C/T).

Example 4

Oligonucleotide Synthesis

Oligonucleotide Synthesis

General method for synthesis of internally labeled oligonucleotides

Oligonucleotide synthesis was performed in the 1 μmol range on an ABI 394 Synthesizer. Commercially available standard phosphoramidites (DMT ibu G, DMT bz A; DMT bz C and DMTrT) and chemicals for standard synthesis were obtained from Glen Research.

For internally modified oligonucleotides phosphate-CPG was used in order to obtain 3' phosphorylated oligonucleotides. The phosphoramidites from Example 1b and 1c were filled in an appropriate bottle, diluted with anhydrous acetonitrile to a conc. of 100 μmol/l and attached to the extra positions of the synthesizer.

a) Synthesis of Internally Modified Oligonucleotide by Using Labeled Phosphoramidite 1b (SEQ ID NO: 05)

For the synthesis the standard ABI program for DNA oligonucleotides was used. Removal of the oligonucleotides from the solid support and deprotection was carried out with 33% $NH_3$ for 8 h at 55° C. The solution was evaporated under vacuum and dissolved in buffer A. The labeled oligonucleotide was purified by reversed phase using an Oligo R3 4.6× 50 mm column Chromatography: buffer A: 0.1 M Triethylammonium acetate in water pH 7.0; buffer B: 0.1 M triethylammonium acetate in water/MeCN 1:1; gradient: 2 min 0% B; in 45 min to 100% B. Resulting fractions were analyzed by a HPLC with a diode array detector. Fractions with purity over 90% and with absorption bands at 260 and 495 were combined. The fractions from the labeled oligonucleotide peaks were collected and the solvent was removed by using a vacuum centrifuge. The remainder was dissolved in double distilled water and then evaporated again with vacuum centrifuge. This procedure was repeated three times. The pellet was dissolved in water and lyophilized.

b) Synthesis of an Internally Modified Oligonucleotide by Using Aminomodified Nitroindole-Phosphoramidite 1c and Postlabeling (SEQ ID NO: 04):

An internal amino group linked to a nitroindole was introduced by using Phosphoramidite described in Example 1c. As solid support 3'-phosphate CPG (GlenResearch 20-2900-01) was used. For the synthesis the standard ABI program for DNA oligonucleotides was used. Removal of the oligonucleotides from the solid support and deprotection was carried out with 33% $NH_3$ for 8 h at 55° C. The solution was evaporated under vacuum. The remainder was dissolved in 600 μl double distilled water and transferred in a microcentrifuge tube 60 μl of sodium acetate buffer (3M, pH=8.5 were added). Upon addition of 1.8 ml cold ethanol the mixture was stored at −15° C. for 3 h. The solution was centrifuged at 10000×g for 15 min. The supernatant was decanted. The pellet is washed with 200 μl cold ethanol. After centrifugation the supernatant was decanted. The pellet was dissolved in 400 μl sodium borate buffer (0.1M, pH 8.5) and was labeled according standard procedures. Therefore a solution of 1 mg of a dye NHS ester (e.g., carboxyfluorescein) in DMF was added and reacted for 15 h. All solvents were removed under high vacuum by using a rotary evaporator. The labeled oligonucleotide was purified as described in Example 1

Example 5

Figure 3:
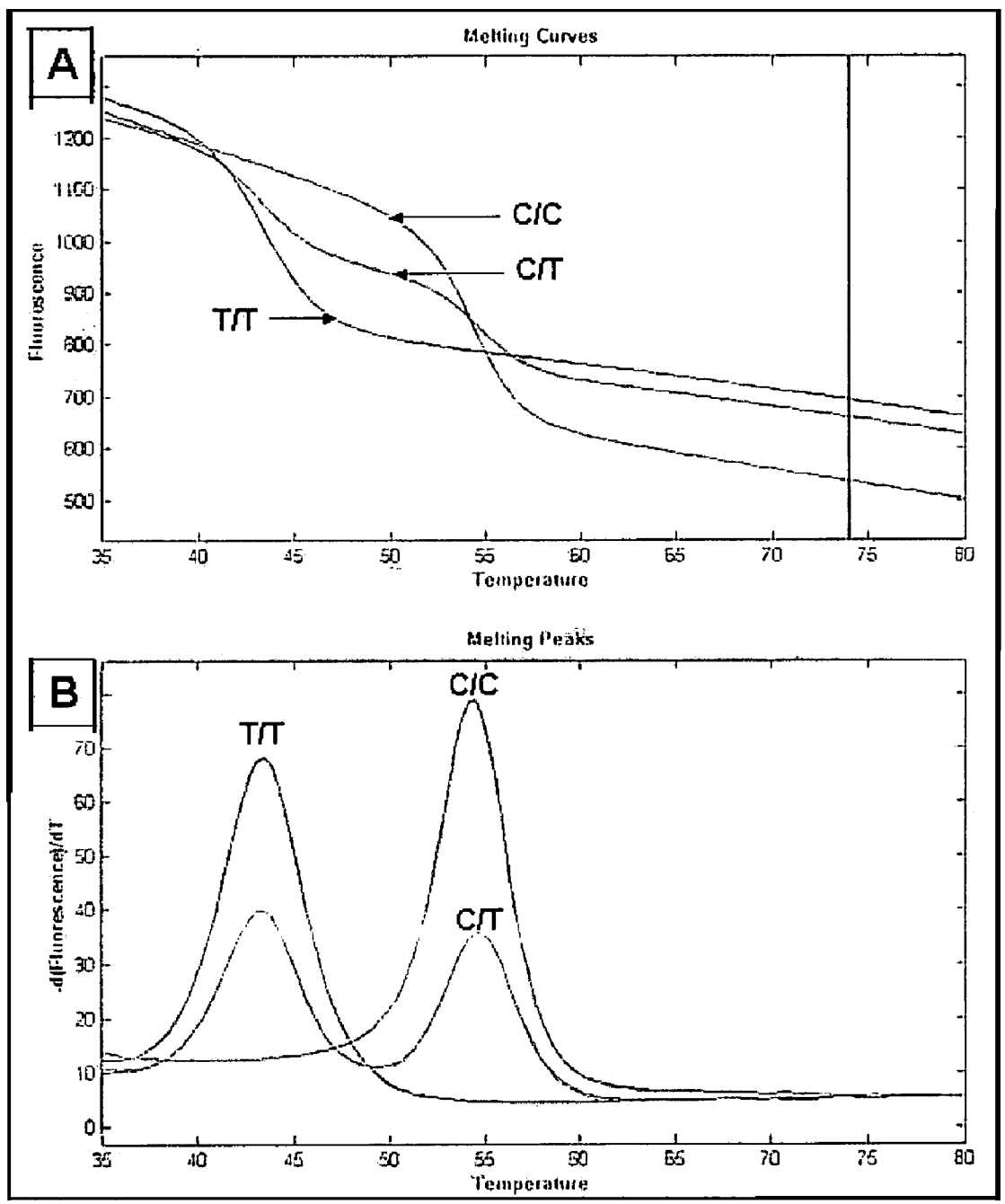
FIG. 3: Fluorescent melting curve analysis using internally FAM-labeled detector oligonucleotide SLP 1 (SEQ ID NO: 04).

Increased Signal Dynamics for Genotyping of the MDR-1 C3435T Polymorphism Using an Internally Fluorescent-Dye Labeled Oligonucleotide Genotyping of the MDR-1 C3435T single nucleotide polymorphism was chosen as test system. As detector probe an oligonucleotide carrying an internal Fluorescent-dye-label was used for melting curve analysis. The labeled internal DNA building block was used as a substitute for a naturally occurring base as described below. The modified detector oligonucleotide could be successfully inserted at various positions in the oligonucleotide sequence and used for SNP genotyping (FIGS. 3 and 4). However, signal dynamics was increased compared to a terminally labeled oligonucleotide (FIG. 4). The internal oligonucleotide building block can also be used to shift Tm values depending on position and substituted nucleotide. As example, strong shifts can be achieved substituting a dG whereas Tm-shifting is decreased when a dA is substituted (Table 2).

Conditions for DNA isolation, PCR and melting curve analysis were essentially the same as described in Example 3.

Sequences of PCR Primers and Detector-Probe:

PCR-primer sense (SEQ ID NO: 01): 5'-d(gatctgtgaactct-tgttttca)-3'

PCR-primer antisense (SEQ ID NO: 02): 5'-d(tttgaa-gagagacttacattaggc)-3'

Single labeled detector probes:

SEQ ID NO: 04: SLP1: 5'-d(tcacagnaagagatcgtgaggg)-p-3'
SEQ ID NO: 05: SLP2: 5'-d(tcacaggangagatcgtgaggg)-p-3'
n: 1-(2-deoxy-beta-D-ribofuranosyl)-5-nitroindole functionalized with 6-carboxyfluorescein, p: phosphate In FIG. 3 melting curves (A) and melting peaks (B) are displayed for each possible genotype of the MDR1 C3435T polymorphism using SLP 1 as detection probe. Tm values were 54.5° C. (C/C homozygous), 43.4° C. (T/T homozygous) and 54.7° C.+43.4° C. (C/T heterozygous).

In FIG. 4 melting curves (A) and melting peaks (B) are compared for an internally labeled detector oligonucleotide SLP2 (curves a, b) versus a 5'-terminal labeled detector oligonucleotide used in Example 3 (curves c, d). Signal enhancement is illustrated for both C/C homozygous DNA (curve a versus c) and T/T homozygous DNA (curves b versus d). Tm values were 58.9° C. (curve a), 49.1° C. (curve b), 66.1° C. (curve c) and 58.4° C. (curve d).

TABLE 2

Comparison of Tm values between terminal and internal labeled oligonucleotides

| Genotype | terminal label/° C. | internal label/° C. dG substitution | internal label/° C. dA substitution |
|---|---|---|---|
| C/C | 66.1 | 54.4 | 58.9 |
| T/T | 58.4 | 43.4 | 49.1 |

---

What is claimed is:

1. A compound having the formula

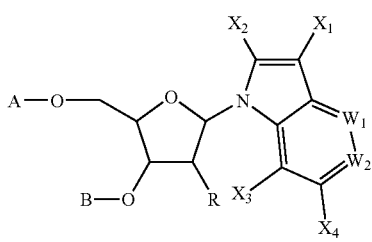

wherein

A is selected from the group consisting of H, phosphate, triphosphate, a protecting group, and a chain of nucleotide tide residues, B is selected from the group consisting of H, a phosphoramidite group, an H-phosphonate, a solid support, and a chain of nucleotide residues, R is selected from the group consisting of H, F, OH, O-alkyl, O-alkenyl, O-alkinyl, and an O-protective group one of $W_1$ and $W_2$ is C—$NO_2$, and the other of $W_1$ and $W_2$ is CH or N, one of $X_1$, $X_2$, $X_3$, and $X_4$ is selected from the group consisting of a reactive group, a protected reactive group, a linker with a reactive group, a linker with a protected reactive group, a signal entity, a protected signal entity, a linker with a signal entity, and a linker with a protected signal entity, and the remaining three of $X_1$, $X_2$, $X_3$, and $X_4$ are each H.

2. A compound according to claim 1 wherein
one of $W_1$ and $W_2$ is C-$NO_2$, and the other of $W_1$ and $W_2$ is CH,
one of $X_1$, $X_2$, $X_3$, $X_4$ is selected from the group consisting of a reactive group, a protected reactive group, a linker group, a protected linker group, and a-signal entity, and the remaining three of $X_1$, $X_2$, $X_3$, and $X_4$ are each H.

3. A compound according to claim 2 wherein $X_1$ is selected from the group consisting of a reactive group, a protected reactive group, a linker group, a protected linker group, and a signal entity, and $X_2$, $X_3$, and $X_4$ are each H.

4. A compound according to claim 2 wherein B is selected from the group consisting of a phosphoramidite group, an H-phosphonate, and a solid support.

5. A compound according to claim 1 wherein B is phosphoramidite or an H-phosphonate, A is a protective group, and R is selected from the group consisting of H, F, O-alkyl, O-alkenyl, O-alkinyl, and an O-protective group.

6. A compound according to claim 5 wherein R is H, $W_2$ is C—$NO_2$, and $W_1$ is CH.

7. A compound according to claim 3 wherein the solid support comprises glass beads.

8. A compound according to claim 1 wherein
one of $X_1$, $X_2$, $X_3$, and $X_4$ is selected from the group consisting of a reactive group, a protected reactive group, a linker group, a protected linker group, and a signal entity, and the remaining three of $X_1$, $X_2$, $X_3$, and $X_4$ are each H,
one of $W_1$ and $W_2$ is C—$NO_2$, and the other of $W_1$ and $W_2$ is CH,
R is H, and
A is dimethoxytrityl or a chain of nucleotide residues.

9. A compound according to claim 8 wherein B is selected from the group consisting of a phosphoramidite group, an H-phosphonate, and a solid support.

10. A compound according to claim 9 wherein the solid support is controlled pore glass (CPG).

11. An oligonucleotide comprising a compound according to claim 1.

12. An oligonucleotide according to claim 11 wherein one of $X_1$, $X_2$, $X_3$, $X_4$ is a signal entity, and the remaining three of $X_1$, $X_2$, $X_3$, and $X_4$ are each H.

13. An oligonucleotide according to claim 12, wherein the signal entity is a fluorescent entity.

14. An oligonucleotide according to claim 13 wherein the oligonucleotide further comprises a second fluorescent entity attached to the oligonucleotide, wherein the second fluorescent entity is different than the other flouresecent entity.

15. A method of synthesizing an oligonucleotide comprising the compound of claim 1, the method comprising the step of
providing a nucleotide,
elongating the nucleotide to provide a chain of nucleotides, and
incorporating a compound into the elongating chain of nucleotides whereby said oligonucleotide is formed, the compound having the formula:

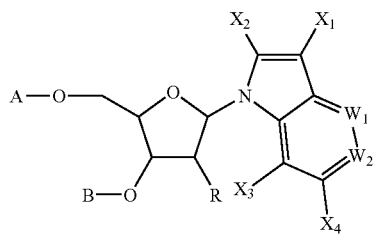

wherein
A is selected from the group consisting of H, phosphate, triphosphate, a protecting group, and a chain of nucleotide residues,
B is selected from the group consisting of a phosphoramidite group, an H-phosphonate, and a solid support,
R is H,
one of $W_1$ and $W_2$ is C—$NO_2$, and the other of $W_1$ and $W_2$ is CH,
one of $X_1$, $X_2$, $X_3$, and $X_4$ is selected from the group consisting of a reactive group, a protected reactive group, a linker group, a protected linker group, and a signal entity, and the remaining three of $X_1$, $X_2$, $X_3$, and $X_4$ are each H.

16. A method of synthesizing an oligonucleotide comprising the compound of claim 1, the method comprising the steps of
providing a nucleotide,
elongating the nucleotide to provide a chain of nucleotides, and
incorporating a compound into the elongating chain of nucleotides during oligonucleotide synthesis, whereby said oligonucleotide is formed, the compound having the formula:

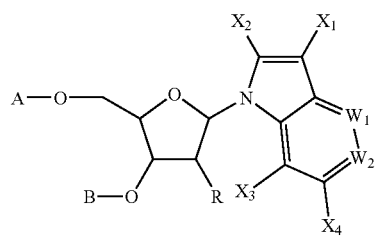

wherein
A is dimethoxytrityl or a chain of nucleotide residues,
B is selected from the group consisting of a phosphoramidite group, an H-phosphonate, and a solid support,
R is H,
one of $W_1$ and $W_2$ is C—$NO_2$, and the other of $W_1$ and $W_2$ is CH,
one of $X_1$, $X_2$, $X_3$, and $X_4$ is selected from the group consisting of a reactive group, a protected reactive group, a linker group, a protected linker group, and a signal entity, and the remaining three of $X_1$, $X_2$, $X_3$, and $X_4$ are each H.

17. The method of claim 15 further comprising the step of: coupling a signal entity to the reactive group.

18. A method of detecting a nucleic acid sequence, the method comprising the steps of contacting the nucleic acid sequence with an oligonucleotide according to claim 12 and detecting the binding of the oligonucleotide with the nucleic acid sequence.

19. The method of claim 18 wherein the signal entity of the oligonucleotide is a fluorescent entity.

20. The method of claim 18 wherein the oligonucleotide comprises a compound having the formula:

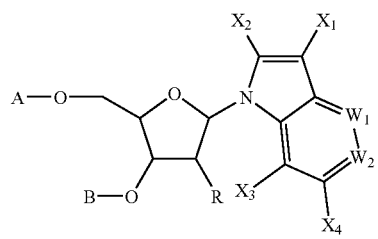

wherein
A is selected from the group consisting of H, phosphate, triphosphate, a protecting group, and a chain of nucleotide residues,
B is selected from the group consisting of H, a phosphoramidite group, an H-phosphonate, a solid support, and a chain of nucleotide residues, R is selected from the group consisting of H, F, OH, O-alkyl, O-alkenyl, O-alkinyl, and an O-protective group, one of $W_1$ and $W_2$ is C—$NO_2$, and the other of $W_1$ and $W_2$ is CH or N, and one of $X_1$, $X_2$, $X_3$, and $X_4$ is a first fluorescent entity, and the remaining three of $X_1$, $X_2$, $X_3$, and $X_4$ are each H, wherein the oligonucleotide further comprises a second fluorescent entity attached to the oligonucleotide, the second fluorescent entity being different than the first fluorescent entity.

* * * * *